(12) United States Patent
Agrafioti et al.

(10) Patent No.: US 9,472,033 B2
(45) Date of Patent: *Oct. 18, 2016

(54) PREAUTHORIZED WEARABLE BIOMETRIC DEVICE, SYSTEM AND METHOD FOR USE THEREOF

(71) Applicant: Nymi Inc., Toronto (CA)

(72) Inventors: Foteini Agrafioti, Toronto (CA); Karl Martin, Toronto (CA); Stephen Oung, Toronto (CA)

(73) Assignee: Nymi Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/162,109

(22) Filed: May 23, 2016

(65) Prior Publication Data
US 2016/0267732 A1   Sep. 15, 2016

Related U.S. Application Data

(63) Continuation of application No. 14/942,919, filed on Nov. 16, 2015, now Pat. No. 9,349,235, which is a continuation of application No. 14/670,316, filed on Mar. 26, 2015, now Pat. No. 9,189,901, which is a
(Continued)

(51) Int. Cl.
*A61B 8/00* (2006.01)
*G05B 19/00* (2006.01)
(Continued)

(52) U.S. Cl.
CPC ................................ *G07C 9/00158* (2013.01)

(58) Field of Classification Search
None
See application file for complete search history.

(56) References Cited

U.S. PATENT DOCUMENTS 5,490,139 A   2/1996   Baker et al.
6,041,410 A   3/2000   Hsu et al.
(Continued)

FOREIGN PATENT DOCUMENTS

WO   2004012388 A1   2/2004
WO   2005117527 A3   4/2006
(Continued)

OTHER PUBLICATIONS

International Search Report and Written Opinion for International Application No. PCT/IB2014/001383 mailed on Dec. 8, 2014, 11 pages.
(Continued)

*Primary Examiner* — Jennifer Mehmood
*Assistant Examiner* — Pameshanand Mahase
(74) *Attorney, Agent, or Firm* — John W. Branch; Lowe Graham Jones PLLC

(57) ABSTRACT

Embodiments are directed towards authenticating users using biometric devices. The biometric device may be arranged to capture one or more biometric feature of a user that may be wearing the biometric device such as biometric features that correspond to an electrocardiogram of the user. The user of the biometric device may be authenticated based on one or more biometric features, or a combination thereof. Authenticating the user of the biometric device, may include communicating information that includes biometric features to an authorized authentication device (AAD). When the user is authenticated, the biometric device may be preauthorized for the user. When the preauthorized biometric device senses at least one access point, an authorization signal may be provided to the access point. If the preauthorized biometric device is removed from the user, the biometric device is deauthorized, disabling access to access points by the user.

30 Claims, 17 Drawing Sheets

Related U.S. Application Data continuation of application No. 14/340,414, filed on Jul. 24, 2014, now Pat. No. 8,994,498.

(60) Provisional application No. 61/858,479, filed on Jul. 25, 2013.

(51) Int. Cl.

| | | |
|---|---|---|
| *A61B 5/02* | (2006.01) | |
| *G06F 21/00* | (2013.01) | |
| *G07C 9/00* | (2006.01) | |

(56) References Cited

U.S. PATENT DOCUMENTS

| | | | |
|---|---|---|---|
| 6,418,424 B1 | 7/2002 | Hoffberg et al. | |
| 6,580,356 B1 | 6/2003 | Alt et al. | |
| 6,799,729 B1 | 10/2004 | Voic | |
| 7,023,320 B2 | 4/2006 | Dvorak | |
| 7,095,707 B2 | 8/2006 | Rakib et al. | |
| 7,378,939 B2 | 5/2008 | Sengupta et al. | |
| 7,689,833 B2 * | 3/2010 | Lange | A61B 5/04525 382/115 |
| 7,780,080 B2 | 8/2010 | Owen et al. | |
| 7,814,332 B2 | 10/2010 | Beenau et al. | |
| 8,352,730 B2 | 1/2013 | Giobbi | |
| 8,371,501 B1 | 2/2013 | Hopkins | |
| 8,412,949 B2 | 4/2013 | Giobbi et al. | |
| 8,468,362 B2 * | 6/2013 | Konetski | G06F 21/32 713/161 |
| 8,869,263 B2 | 10/2014 | Pasquero et al. | |
| 8,994,498 B2 * | 3/2015 | Agrafioti | G06F 21/40 340/5.52 |
| 9,189,901 B2 * | 11/2015 | Agrafioti | G06F 21/40 |
| 9,349,235 B2 * | 5/2016 | Agrafioti | G06F 21/40 |
| 2002/0140542 A1 | 10/2002 | Prokoski et al. | |
| 2003/0046228 A1 | 3/2003 | Berney | |
| 2003/0135097 A1 | 7/2003 | Wiederhold et al. | |
| 2005/0068171 A1 | 3/2005 | Kelliher et al. | |
| 2007/0016088 A1 | 1/2007 | Grant et al. | |
| 2007/0049267 A1 | 3/2007 | Kota et al. | |
| 2007/0063548 A1 | 3/2007 | Eipper | |
| 2007/0177770 A1 | 8/2007 | Derchak et al. | |
| 2007/0186105 A1 | 8/2007 | Bailey et al. | |
| 2008/0091681 A1 | 4/2008 | Dwivedi et al. | |
| 2008/0216171 A1 | 9/2008 | Sano et al. | |
| 2008/0253626 A1 | 10/2008 | Shuckers et al. | |
| 2008/0294907 A1 * | 11/2008 | Hively | A61B 5/04012 713/186 |
| 2009/0037983 A1 | 2/2009 | Chiruvolu et al. | |
| 2009/0146947 A1 | 6/2009 | Ng | |
| 2009/0199264 A1 | 8/2009 | Lang | |
| 2010/0030695 A1 | 2/2010 | Chen et al. | |
| 2010/0306106 A1 * | 12/2010 | Dagan | G06F 21/32 705/43 |
| 2010/0311482 A1 | 12/2010 | Lange | |
| 2012/0004523 A1 | 1/2012 | Richter et al. | |
| 2012/0060030 A1 | 3/2012 | Lamb | |
| 2012/0123232 A1 | 5/2012 | Najarian et al. | |
| 2012/0198277 A1 | 8/2012 | Busser et al. | |
| 2012/0316406 A1 | 12/2012 | Rahman et al. | |
| 2012/0317024 A1 | 12/2012 | Rahman et al. | |
| 2013/0159021 A1 | 6/2013 | Felsher | |
| 2013/0322622 A1 | 12/2013 | Bailey et al. | |
| 2014/0188770 A1 | 7/2014 | Agrafioti et al. | |
| 2015/0028996 A1 | 1/2015 | Agrafioti et al. | |

FOREIGN PATENT DOCUMENTS

| | | |
|---|---|---|
| WO | 2007128975 A2 | 11/2007 |
| WO | 2012151680 A1 | 11/2012 |

OTHER PUBLICATIONS

Official Communication for U.S. Appl. No. 14/461,881 mailed on Oct. 27, 2014 (18 pages).

Agrafioti et al., "Medical Biometrics in Mobile Health Monitoring," Security and Communication Networks, 2011, 4, pp. 525-539.

Hoekema et al., "Geometrical Aspects of the Interindividual Variability of Multilead ECG Recordings," IEEE Transactions on Biometrical Engineering, vol. 48, No. 5, May 2001, pp. 551-559.

Draper et al., "The Corrected Orthogonal Electrocardiogram and Vectorcardiogram in 510 Normal Men (Frank Lead System)" Circulation, vol. 30, 1964, pp. 853-864.

Biel et al., "ECG Analysis: A New Approach in Human Identification," IEEE Transactions on Instrumentation and Measurement, vol. 50, No. 3, Jun. 2001, pp. 808-812.

Wubbeler et al., "Verification of Humans Using the Electrocardiogram," Pattern Recognition Letter, vol. 28, No. 10, 2007, pp. 1172-1175.

Odinaka et al., "ECG Biometrics: A Robust Short-time Frequency Analysis," Proceedings of IEEE International Workshop on Information Forensics and Security, Dec. 2010, pp. 1-6.

Li et al., "Robust ECG Biometrics by Fusing Temporal and Cepstral Information," Proceedings of 20th International Conference on Pattern Recognition, Aug. 2010, pp. 1326-1329.

Agrafioti et al., "ECG Based Recognition Using Second Order Statistics," Communication Networks and Services Research Conference, May 2008, pp. 82-87.

Agafioti et al., "Heart Biometrics: Theory, Methods, and Applications," Intech, www.intechopen.com, 19 pages.

Agrafioti et al., "Signal Validation for Cardiac Biometrics," IEEE 35th International Conference on Acoustics, Speech, and Signal Processing, 2010, pp. 1734-1737.

Zhao et al., "Fingerprint Image Synthesis Based on Statistical Feature Models," IEEE 5th International Conference on Biometrics: Theory, Applications, and Systems, 2012, pp. 23-30.

Agrafioti et al., "Medical Biometrics: The Perils of Ignoring Time Dependency," Proceedings of 3rd International Conference on Biometrics: Theory, Applications, and Systems, 2009, pp. 1-6.

Odinaka et al., "ECG Biometric Recognition: A Comparative Analysis" IEEE Transactions on Information Forensics and Security, vol. 7, No. 6, Dec. 2012, pp. 1812-1824.

Bellare et al., "Forward-Security in Private-Key Cryptography," Department of Computer Science and Engineering, 2003, pp. 1-24.

International Search Report for Application No. PCT/CA2012/000448 dated Aug. 23, 2012 (4 pages).

Wang et al., "Analysis of Human Electrocardiogram for Biometric Recognition", EURASIP Journal on Advances in Signal Processing, vol. 2008, Article 10 148658, pp. 1-11, Jan. 31, 2008.

Klosterman et al. "Secure Continuous Biometric-Enhanced Authentication", CMU-CS-00-134, School of Computer Science, Carnegie Mellon University, pp. 1-22, May 31, 2000.

Ortega-Garcia, et al., "MCYT Baseline Corpus: A Bimodal Biometric Database", IEE Proc.—Vis. Image Signal Process, vol. 150, No. 6, pp. 395-401. Dec. 31, 2003.

Pasini et al., "Sas-based Authenticated Key Agreement," In Public Key Cryptography—PKC 2006, pp. 395-409, Springer, 2006.

Official Communication for U.S. Appl. No. 14/675,489 mailed on Jun. 11, 2015 (24 pages).

Noble et al.. "The Case for Transient Authentication," Department of Electrical Engineering and Computer Science, University of Michigan, Ann Arbor, MI, 6 pages.

Ojala et al., "Wearable Authentication Device for Transparent Login in Nomadic Applications Environment," 2008 International Conference on Signals, Circuits and Systems, 6 pages.

Al-Muhtadi et al., "Wearable Security Services," Department of Computer Science, 6 pages.

Official Communication for U.S. Appl. No. 14/340,414 mailed on Jan. 22, 2015 (15 pages).

Supplementary European Search report and Search Opinion for EP application 12782151.0 mailed on Mar. 12, 2015 (7 pages).

Official Communication for U.S. Appl. No. 14/461,881 mailed on Feb. 12, 2015 (28 pages).

Official Communication for U.S. Appl. No. 14/675,489 mailed on Sep. 28, 2015 (11 pages).

Official Communication for U.S. Appl. No. 14/670,316 mailed on May 8, 2015 (20 pages).

(56) References Cited

OTHER PUBLICATIONS

Official Communication for U.S. Appl. No. 14/670,316 mailed on Aug. 31, 2015 (9 pages).
Official Communication for U.S. Appl. No. 14/949,509 mailed on Feb. 2, 2016 (17 pages).
Official Communication for U.S. Appl. No 14/942,919 mailed on Mar. 30, 2016 (14 pages).
Official Communication for U.S. Appl. No. 14/116,058 mailed on Mar. 25, 2016 (19 pages).
Official Communication for U.S. Appl. No. 14/949,509 mailed Jun. 7, 2016, (11 pages).
Official Communication for U.S. Appl. No. 14/116,058 mailed on Jul. 12, 2016, (16 pages).
European Search Report for Application No. 16162764.1, mailed Aug. 5, 2016, 9 pages.

* cited by examiner

PREAUTHORIZED WEARABLE BIOMETRIC DEVICE, SYSTEM AND METHOD FOR USE THEREOF

CROSS-REFERENCE TO RELATED APPLICATIONS

This Utility Patent Application is a Continuation of U.S. patent application Ser. No. 14/942,919 filed on Nov. 16, 2015, now U.S. Pat. No. 9,349,235 issued on May 24, 2016, which is a Continuation of U.S. patent application Ser. No. 14/670,316 filed on Mar. 26, 2015, now U.S. Pat. No. 9,189,901 issued on Nov. 17, 2015, which is a Continuation of U.S. patent application Ser. No. 14/340,414 filed on Jul. 24, 2014, now U.S. Pat. No. 8,994,498 issued on Mar. 31, 2015, which is based on U.S. Provisional Patent Application No. 61/858,479, filed on Jul. 25, 2013, entitled "PREAUTHORIZED WEARABLE BIOMETRIC DEVICE, SYSTEM AND METHOD FOR USE THEREOF," the benefits of which are claimed under 35 U.S.C. §120 and §119(e), and which are each further incorporated in entirety by reference.

FIELD OF THE INVENTION

The present invention pertains to biometric authentication of a user, and more particularly but not exclusively, to a method for user authentication that separates biometric identity authentication from access control.

BACKGROUND

Identity authentication for access control as well as personalization of the environment is a key capability tied to many aspects of daily life, and is becoming even more vital with increasingly personalized technology offerings. Some methods for identity authentication can add varying levels of friction to our daily lives. In some cases, the cumulative friction that authentication mechanisms cause in user's daily lives may be causing significant difficulty and inconvenience for users. In the case of physical items, such as keys and cards, users may be carrying an ever-increasing load in their pockets and bags, having to dig out various items throughout the day. In the case of passwords and PINs, user's online accounts and smart devices may require them, but remembering them while also making them sufficiently secure has become an elusive goal. Furthermore, these items, physical or digital, may be stolen or copied. Modern biometric devices have promised a world of automatic and seamless identification, however the practical realities result in trade-offs between security/accuracy and convenience. The trade-off may be tolerable when examining a single instance use of these technologies, but the trade-off becomes increasingly intolerable when the technology is utilized multiple times throughout the day, for every interaction that requires identity authentication i.e., every time you unlock your smart phone, unlock your car, pay by credit or debit, access your office building, access your office computer system, etc. Thus, it is with respect to these and other considerations that these innovations are made.

BRIEF DESCRIPTION OF THE FIGURES

Non-limiting and non-exhaustive embodiments of the present innovations are described with reference to the following drawings. In the drawings, like reference numerals refer to like parts throughout the various figures unless otherwise specified. For a better understanding of the present innovations, reference will be made to the following Description of the Various Embodiments, which is to be read in association with the accompanying drawings, wherein.

DETAILED DESCRIPTION OF THE INVENTION

Figure 1:
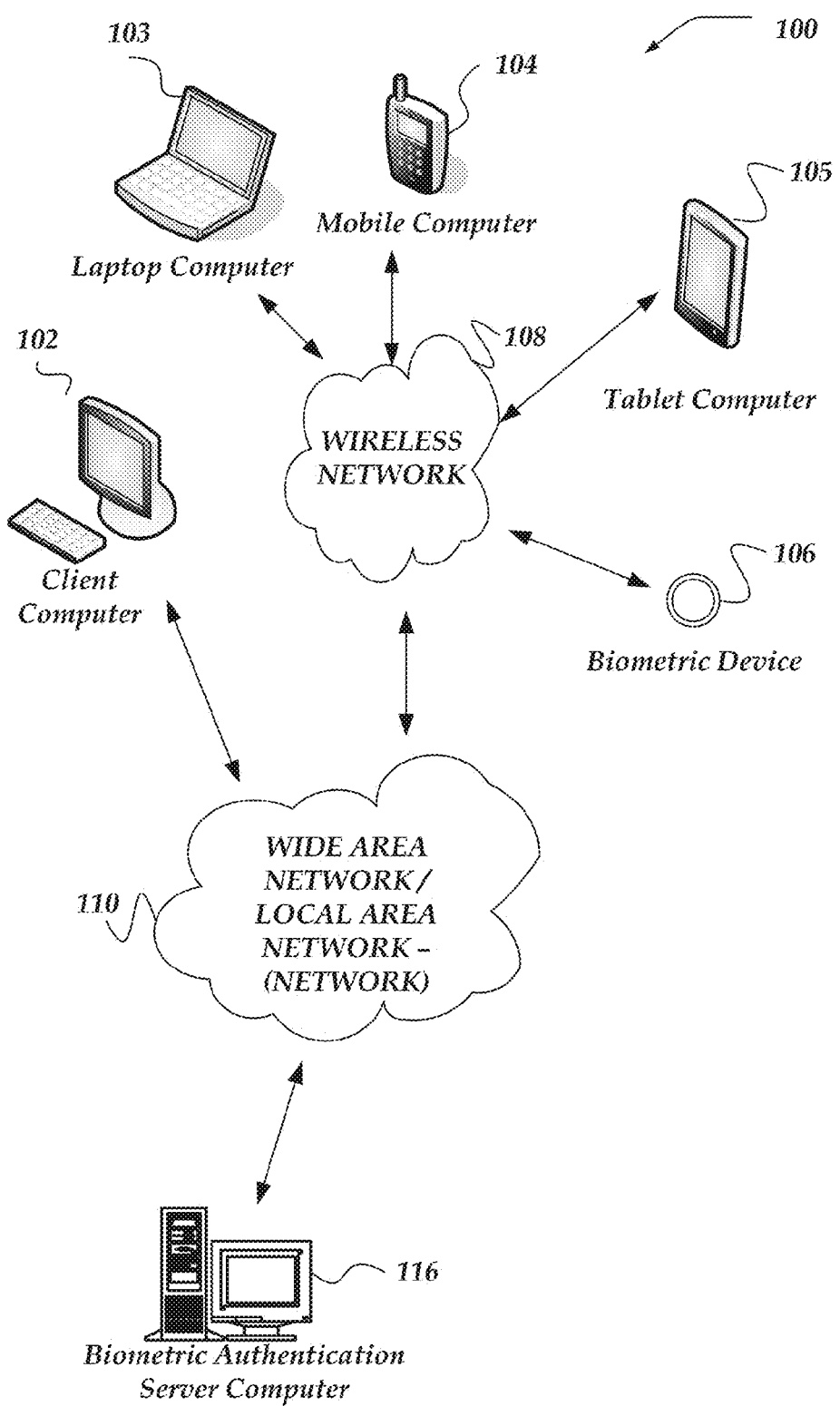
FIG. 1 shows components of one embodiment of an environment in which embodiments of the invention may be practiced.

The present innovations now will be described more fully hereinafter with reference to the accompanying drawings, which form a part hereof, and which show, by way of illustration, specific embodiments by which the innovations may be practiced. These innovations may, however, be embodied in many different forms and should not be construed as limited to the embodiments set forth herein; rather, these embodiments are provided so that this disclosure will be thorough and complete, and will fully convey the various embodiments to at least those skilled in the art. Among other things, the present innovations may be embodied as methods, computers, or devices. Accordingly, the embodiments may take the form of an entirely hardware embodiment, an entirely software embodiment or an embodiment combining software and hardware aspects. The following detailed description is, therefore, not to be taken in a limiting sense.

Unless defined otherwise, all technical and scientific terms used herein have the same meaning as commonly understood by one of ordinary skill in the art to which this invention belongs.

Throughout the specification and claims, the following terms take the meanings explicitly associated herein, unless the context clearly dictates otherwise. The phrase "In one of the embodiments" or "in at least one of the various embodiments" as used herein does not necessarily refer to the same embodiment, though it may. Furthermore, the phrase "in another embodiment" or "in some embodiments" as used herein does not necessarily refer to a different embodiment, although it may. Thus, as described below, various embodiments may be readily combined, without departing from the scope or spirit of the innovations disclosed herein.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

The terms "biometric," "biometric data," or "biometric signal" as used herein are understood to mean any signal that can be obtained from a user that can uniquely identify the user. Non-limiting examples of biometric signals are gait, heart rate, galvanic skin response, temperature, fingerprint, voice or voiceprint, body electrical characteristic, body thermal characteristic, iris pattern, vein pattern, eye vein pattern, facial or other anatomical structure, electrocardiogram, photoplethysmogram, electromyogram, electroencephalogram, transient otoacoustic emissions, phonocardiogram, DNA, one or more chemical markers, one or more biochemical markers, skin-color variation or discolouration, perspiration, or a combination thereof. A unique identity of a user can also be obtained by observing patterns or combinations of more one biometric characteristic. For example a person may have a unique heart rate at a particular temperature and with a particular amount of sweat. In this way, two or more biometric observations can be combined or fused to obtain a multi-modal unique biometric profile. This is especially useful in situations wherein one particular biometric is not sufficient as a standalone identifier. In one example, perspiration and gait can be combined or fused to provide a unique biometric profile for a user. Information from sources that are standalone identifiers can also be combined in order to increase accuracy and/or security. In another example, a multi-modal biometric system may fuse fingerprints with iris and face characteristics.

The term "access point" as used herein refers to any logical or physical gateway, device, or application that requires authorization, such as for security or personalization purposes, and is otherwise locked or inaccessible to the user. Some non-limiting examples of physical access points are electronically locked doors, parking transceivers, smart environment technologies, vehicle doors and transit systems. Some non-limiting examples of logical access points are password, PIN or passcode protected electronic devices or accounts, proof of payment systems, point of sale stations, automated bank teller machines, library checkout systems, and hotel and airport check-in stations.

The term "control signal" as used herein refers to the signal sent by a biometric device to a physical or logical access point that may enable the user to unlock or access the access point. The control signal may be a binary encoded sequence transmitted wired or wirelessly using but not limited to bluetooth, near field communication or Wifi. The control signal is preferably a non-biometric signal, however it can also be a biometric signal if the access control at the access point requires it.

The following briefly describes the embodiments of the invention in order to provide a basic understanding of some aspects of the invention. This brief description is not intended as an extensive overview. It is not intended to identify key or critical elements, or to delineate or otherwise narrow the scope. Its purpose is merely to present some concepts in a simplified form as a prelude to the more detailed description that is presented later.

Briefly stated, various embodiments are directed towards authenticating users using biometric devices. In at least one of the various embodiments, the biometric device may be arranged to capture one or more biometric feature of a user that may be wearing the biometric device. In at least one of the various embodiments, capturing biometric features of the user of the biometric device, may include, capturing one or more biometric features that correspond to an electrocardiogram of the user.

In at least one of the various embodiments, the user of the biometric device may be authenticated based on one or more biometric features, or a combination thereof. In at least one of the various embodiments, authenticating the user of the biometric device, may also include: communicating information that includes biometric features to an authorized authentication device (AAD) that may be separate from the biometric device; and comparing the biometric features to a biometric profile that corresponds to the user and is stored on the AAD, such that the biometric device may be preauthorized for the user if the biometric profile stored on the AAD corresponds to one or more of the user's biometric features.

Further, in at least one of the various embodiments, when the user is authenticated, the biometric device may be preauthorized for the user. Also, in at least one of the various embodiments, when the preauthorized biometric device senses at least one access point, an authorization signal may be provided to the access point. In at least one of the various embodiments, preauthorizing the biometric device for the user, may also include, providing a list of one or more access points that the user may be permitted to access based profile information that may be associated with the user and/or profile information that may be associated with the access point.

In at least one of the various embodiments, authorizing a user that may be preauthorized by the biometric device to access an access point, may include, authorizing the user to access the access point based on providing additional information and/or meeting additional conditions, such as, a password, a Personal Identification Number (PIN), a gesture, a voice command, a finger tap, a distance between the preauthorized biometric device and the at least access point, one or more additional biometric features of the user, or the like, or combination thereof.

Further, in at least one of the various embodiments, the user may be provided access to the access point based on an affirmative confirmation of the authorization signal by the access point. Also, in at least one of the various embodiments, if the preauthorized biometric device is removed from the user, the biometric device may be deauthorized for the user such that access to access points by the user may be disabled.

Also, in at least one of the various embodiments, if two or more access points are sensed by the preauthorized biometric device, one or more of the two or more access points may be determined for enabling access for the user based on at least one secondary condition.

In at least one of the various embodiments, an administrative user may be enabled to provide profile information for a plurality of users of the biometric device. And, in at least one of the various embodiments, enabling access for that user to access points based at least on the user profile information for the authenticated users.

Illustrative Operating Environment

FIG. 1 shows components of one embodiment of an environment in which embodiments of the invention may be practiced. Not all of the components may be required to practice the invention, and variations in the arrangement and type of the components may be made without departing from the spirit or scope of the invention. As shown, system 100 of FIG. 1 includes local area networks (LANs)/wide area networks (WANs)—(network) 110, wireless network 108, client computers 102-105, biometric device 106, biometric authentication server computer 116, or the like.

At least one embodiment of client computers 102-105 is described in more detail below in conjunction with FIG. 2. In one embodiment, at least some of client computers 102-105 may operate over one or more wired and/or wireless networks, such as networks 108, and/or 110. Generally, client computers 102-105 may include virtually any computer capable of communicating over a network to send and receive information, perform various online activities, offline actions, or the like. In one embodiment, one or more of client computers 102-105 may be configured to operate within a business or other entity to perform a variety of services for the business or other entity. For example, client computers 102-105 may be configured to operate as a web server, firewall, client application, media player, mobile telephone, game console, desktop computer, access point, authorized authentication device (AAD), or the like. However, client computers 102-105 are not constrained to these services and may also be employed, for example, as for end-user computing in other embodiments. It should be recognized that more or less client computers (as shown in FIG. 1) may be included within a system such as described herein, and embodiments are therefore not constrained by the number or type of client computers employed.

Computers that may operate as client computer 102 may include computers that typically connect using a wired or wireless communications medium such as personal computers, multiprocessor systems, microprocessor-based or programmable electronic devices, network PCs, or the like. In some embodiments, client computers 102-105 may include virtually any portable computer capable of connecting to another computer and receiving information such as, laptop computer 103, mobile computer 104, tablet computers 105, or the like. However, portable computers are not so limited and may also include other portable computers such as cellular telephones, display pagers, radio frequency (RF) devices, infrared (IR) devices, Personal Digital Assistants (PDAs), handheld computers, wearable computers, integrated devices combining one or more of the preceding computers, or the like. As such, client computers 102-105 typically range widely in terms of capabilities and features. Moreover, client computers 102-105 may access various computing applications, including a browser, or other web-based application.

A web-enabled client computer may include a browser application that is configured to receive and to send web pages, web-based messages, and the like. The browser application may be configured to receive and display graphics, text, multimedia, and the like, employing virtually any web-based language, including a wireless application protocol messages (WAP), and the like. In one embodiment, the browser application is enabled to employ Handheld Device Markup Language (HDML), Wireless Markup Language (WML), WMLScript, JavaScript, Standard Generalized Markup Language (SGML), HyperText Markup Language (HTML), eXtensible Markup Language (XML), JavaScript Object Notation (JSON), or the like, to display and send a message. In one embodiment, a user of the client computer may employ the browser application to perform various activities over a network (online). However, another application may also be used to perform various online activities.

Client computers 102-105 also may include at least one other client application that is configured to receive and/or send content between another computer. The client application may include a capability to send and/or receive content, or the like. The client application may further provide information that identifies itself, including a type, capability, name, and the like. In one embodiment, client computers 102-105 may uniquely identify themselves through any of a variety of mechanisms, including an Internet Protocol (IP) address, a phone number, Mobile Identification Number (MIN), an electronic serial number (ESN), or other device identifier. Such information may be provided in a network packet, or the like, sent between other client computers, biometric authentication server computer 116, or other computers.

Client computers 102-105 may further be configured to include a client application that enables an end-user to log into an end-user account that may be managed by another computer, such as biometric authentication server computer 116, or the like. Such an end-user account, in one non-limiting example, may be configured to enable the end-user to manage one or more online activities, including in one non-limiting example, project management, system administration, configuration management, search activities, social networking activities, browse various websites, communicate with other users, or the like.

Biometric device 106 can be any device that can be worn by a user and is capable of obtaining a biometric signal. Non-limiting examples of suitable wearable biometric devices are a wristband, wristwatch, bracelet, necklace, ring, belt, glasses, clothing, hat, headband or earring(s), or any other wearable item that is capable of obtaining a biometric signal. The biometric device 106 can also be incorporated into clothing. In another embodiment, the biometric device 106 may comprise more than one biometric sensor. Biometric device 106 may be arranged to communicate with one or more of client computer 102-105 over a network, such as wireless network 108. Further, biometric device 106 may be arranged to communicate with biometric authentication server computer 116, and/or a cloud computing environment over a network.

Briefly, in some embodiments, biometric device 106 may include wearable devices that may be preauthorized and/or authenticated for a user that is wearing the device. In at least one of the various embodiments, the biometric device may be preauthorized based on one or more biometric features of the user. Further, in at least one of the various embodiments, additional factors, such as, passwords, PINs, user input, or the like, or combination thereof, may also be employed for preauthorization and/or authentication of the devices. Also, in some embodiments, the biometric device, though referred to herein for brevity as a biometric device, may be preauthorized and/or authenticated using factors absent biometric information. In some cases, the device may be arranged to omit biometric sensors capturing biometric features of the users, and instead rely on other security factors.

In at least one of the various embodiments, the biometric device may be arranged to remain preauthorized and/or authenticated as long as the device is worn by user, or otherwise is not separated from the user. Removing the device and/or separating an authenticated and/or preauthorized device from a user will reset the device returning it to an unauthenticated and/or unauthorized state. Additional details biometric devices are described below.

Wireless network 108 is configured to couple client computers 103-105 and biometric device 106 with network 110. Wireless network 108 may include any of a variety of wireless sub-networks that may further overlay stand-alone ad-hoc networks, and the like, to provide an infrastructure-oriented connection for client computers 103-105 and/or biometric device 106. Such sub-networks may include mesh networks, Wireless LAN (WLAN) networks, cellular networks, and the like. In one embodiment, the system may include more than one wireless network.

Wireless network 108 may further include an autonomous system of terminals, gateways, routers, and the like connected by wireless radio links, and the like. These connectors may be configured to move freely and randomly and organize themselves arbitrarily, such that the topology of wireless network 108 may change rapidly.

Wireless network 108 may further employ a plurality of access technologies including 2nd (2G), 3rd (3G), 4th (4G) 5th (5G) generation radio access for cellular systems, WLAN, Wireless Router (WR) mesh, and the like. Access technologies such as 2G, 3G, 4G, 5G, and future access networks may enable wide area coverage for mobile computers, such as client computers 103-105, and biometric device 106 with various degrees of mobility. In one non-limiting example, wireless network 108 may enable a radio connection through a radio network access such as Global System for Mobil communication (GSM), General Packet Radio Services (GPRS), Enhanced Data GSM Environment (EDGE), code division multiple access (CDMA), time division multiple access (TDMA), Wideband Code Division Multiple Access (WCDMA), High Speed Downlink Packet Access (HSDPA), Long Term Evolution (LTE), and the like. In essence, wireless network 108 may include virtually any wireless communication mechanism by which information may travel between client computers 103-105, biometric device 106, and another computer, network, a cloud-based network, a cloud instance, or the like.

Network 110 is configured to couple network computers with other computers, including, biometric authentication service computer 116, client computers 102-105, biometric device 106 through wireless network 108, or the like. Network 110 is enabled to employ any form of computer readable media for communicating information from one electronic device to another. Also, network 110 can include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another. In addition, communication links within LANs typically include twisted wire pair or coaxial cable, while communication links between networks may utilize analog telephone lines, full or fractional dedicated digital lines including T1, T2, T3, and T4, and/or other carrier mechanisms including, for example, E-carriers, Integrated Services Digital Networks (ISDNs), Digital Subscriber Lines (DSLs), wireless links including satellite links, or other communications links known to those skilled in the art. Moreover, communication links may further employ any of a variety of digital signaling technologies, including without limit, for example, DS-0, DS-1, DS-2, DS-3, DS-4, OC-3, OC-12, OC-48, or the like. Furthermore, remote computers and other related electronic devices could be remotely connected to either LANs or WANs via a modem and temporary telephone link. In one embodiment, network 110 may be configured to transport information of an Internet Protocol (IP).

Additionally, communication media typically embodies computer readable instructions, data structures, program modules, or other transport mechanism and includes any information delivery media. By way of example, communication media includes wired media such as twisted pair, coaxial cable, fiber optics, wave guides, and other wired media and wireless media such as acoustic, RF, infrared, and other wireless media.

One embodiment of biometric authentication server computer 116 is described in more detail below in conjunction with FIG. 3. Briefly, however, biometric authentication server computer 116 includes virtually any network computer capable of performing actions for storing, authenticating, processing of biometric information, users, access points, or the like.

Although FIG. 1 illustrates biometric authentication server computer 116 as a single computer, the innovations and/or embodiments are not so limited. For example, one or more functions of biometric authentication server computer 116 may be distributed across one or more distinct network computers. Moreover, biometric authentication server computer 116 is not limited to a particular configuration such as the one shown in FIG. 1. Thus, in one embodiment, biometric authentication server computer 116 may be implemented using a plurality of network computers and/or client computer. In other embodiments, development computer may operate as a plurality of network computers within a cluster architecture, a peer-to-peer architecture, or the like. Further, in at least one of the various embodiments, biometric authentication server computer 116 may be implemented using one or more cloud instances in one or more cloud networks.

Described herein is a security system, method and device that separates user identity authentication from the electronic transactions that rely on user identity authentication. The presently described system of user authentication separates identity authentication from use at an access point by first authenticating a wearable biometric device with an authorized authentication device, thus enabling the identity of a user wearing a preauthorized wearable biometric device to gain later secure access to other systems and devices at one or more access points.

The present system for user authentication is centered around a wearable biometric device that authenticates the wearer based on one or more unique biometric characteristics. The syncing of the wearable biometric device with a pre-initialized authorized authentication device (AAD) authenticates the identity of the user and authorizes the wearable biometric device to wirelessly communicate the preauthenticated user identity to other devices and systems. This may enable logical and physical access by the user at one or more access point as a result of a single biometric authorization with the authorized authentication device. In this way a user can be pre-authenticated using the wearable biometric device and subsequently enable seamless physical and/or logical access control to various devices, systems and spaces.

In contrast, traditional biometric access systems, both wearable and not, require that the user be biometrically authenticated each time the user wishes to gain access to a system. From a technology point of view, this traditional authentication processes can either be an on-device authentication or an off-device authentication. In an on-device authentication, the wearable device can collect and process the biometric signal as a standalone solution. The biometric template is stored locally on the device which performs a biometric matching and verifies the identity of the user. A control signal that signifies an authenticated user is then transmitted to devices and systems at access points that need to be unlocked. In an off-device authentication, the wearable device collects the biometric signal but does not have the power to process it. It transmits the obtained biometric signal, either wired or wirelessly, to a nearby terminal which is responsible for performing the biometric matching. In the case of an off-device authentication, the biometric template can be made directly available to the terminal from a central database or by simply transferring it from the device as well, and the terminal is generally not a personal device, but an institutional system.

The present system provides a compelling security solution as it encompasses a three-factor authentication system whereby: the biometric signal is one authentication factor, the possession of the wearable biometric device is a second authentication factor, and the possession of the AAD is the third authentication factor. In addition, the presently described system allows for faster access control since the user does not require authentication every time she needs to access a physical or logical system. With the present system, the wearable biometric device also has inherently lower processing requirements which allow for lower power consumption.

Illustrative Client Computer

Figure 2:
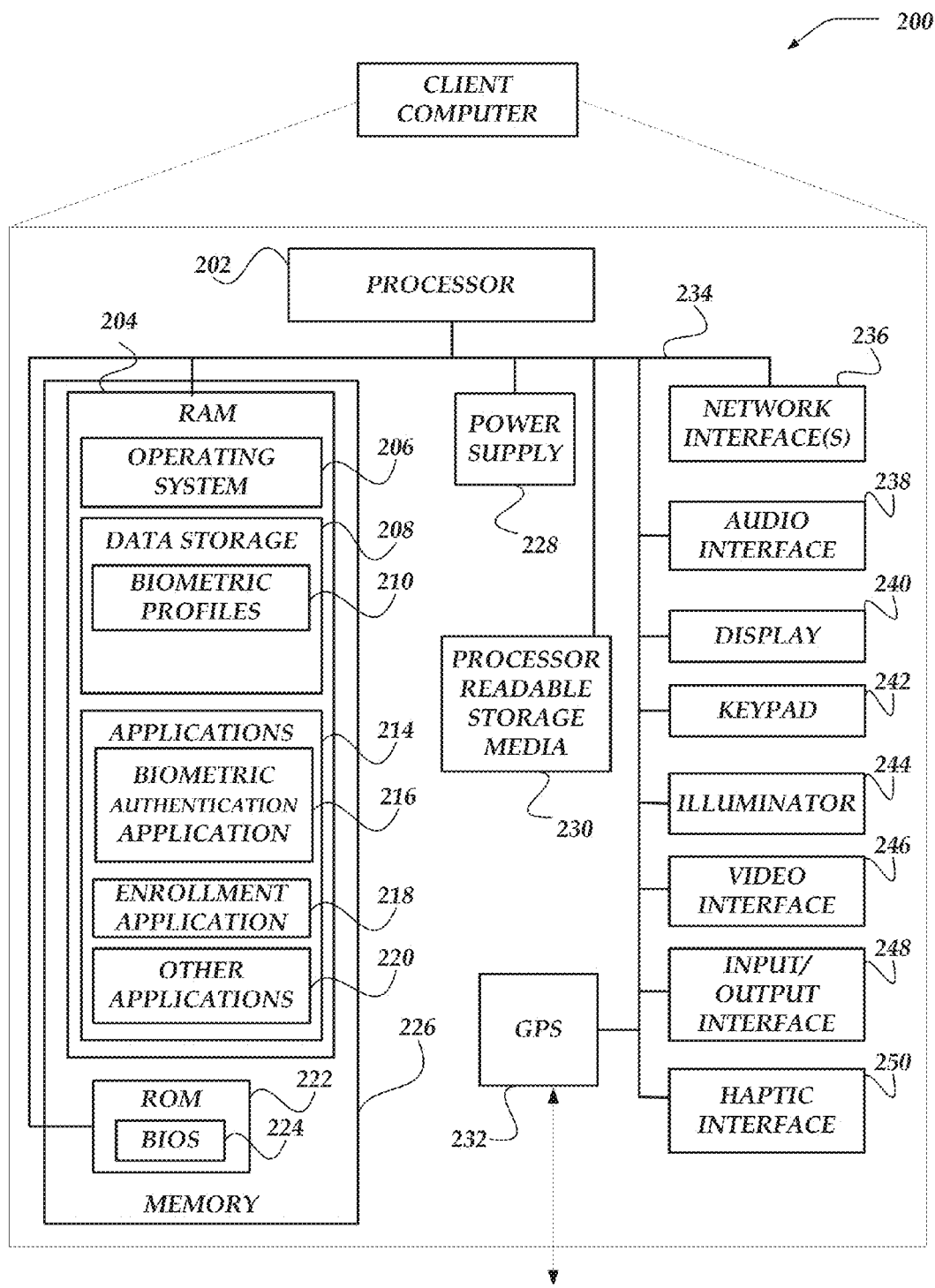
FIG. 2 shows one embodiment of a client computer that may be included in a system in accordance with at least one of the various embodiments.

FIG. 2 shows one embodiment of client computer 200 that may be included in a system in accordance with at least one of the various embodiments. Client computer 200 may include many more or less components than those shown in FIG. 2. However, the components shown are sufficient to disclose an illustrative embodiment for practicing the present invention. Client computer 200 may represent, for example, one embodiment of at least one of client computers 102-105 of FIG. 1.

As shown in the figure, client computer 200 includes a processor 202 in communication with a mass memory 226 via a bus 234. In some embodiments, processor 202 may include one or more central processing units (CPU). Client computer 200 also includes a power supply 228, one or more network interfaces 236, an audio interface 238, a display 240, a keypad 242, an illuminator 244, a video interface 246, an input/output interface 248, a haptic interface 250, and a global positioning system (GPS) receiver 232.

Power supply 228 provides power to client computer 200. A rechargeable or non-rechargeable battery may be used to provide power. The power may also be provided by an external power source, such as an alternating current (AC) adapter or a powered docking cradle that supplements and/or recharges a battery.

Client computer 200 may optionally communicate with a base station (not shown), or directly with another computer. Network interface 236 includes circuitry for coupling client computer 200 to one or more networks, and is constructed for use with one or more communication protocols and technologies including, but not limited to, GSM, CDMA, TDMA, GPRS, EDGE, WCDMA, HSDPA, LTE, user datagram protocol (UDP), transmission control protocol/Internet protocol (TCP/IP), short message service (SMS), WAP, ultra wide band (UWB), IEEE 802.16 Worldwide Interoperability for Microwave Access (WiMax), session initiated protocol/real-time transport protocol (SIP/RTP), or any of a variety of other wireless communication protocols. Network interface 236 is sometimes known as a transceiver, transceiving device, or network interface card (NIC).

Audio interface 238 is arranged to produce and receive audio signals such as the sound of a human voice. For example, audio interface 238 may be coupled to a speaker and microphone (not shown) to enable telecommunication with others and/or generate an audio acknowledgement for some action.

Display 240 may be a liquid crystal display (LCD), gas plasma, light emitting diode (LED), organic LED, or any other type of display used with a computer. Display 240 may also include a touch sensitive screen arranged to receive input from an object such as a stylus or a digit from a human hand.

Keypad 242 may comprise any input device arranged to receive input from a user. For example, keypad 242 may include a push button numeric dial, or a keyboard. Keypad 242 may also include command buttons that are associated with selecting and sending images.

Illuminator 244 may provide a status indication and/or provide light. Illuminator 244 may remain active for specific periods of time or in response to events. For example, when illuminator 244 is active, it may backlight the buttons on keypad 242 and stay on while the client computer is powered. Also, illuminator 244 may backlight these buttons in various patterns when particular actions are performed, such as dialing another client computer. Illuminator 244 may also cause light sources positioned within a transparent or translucent case of the client computer to illuminate in response to actions.

Video interface 246 is arranged to capture video images, such as a still photo, a video segment, an infrared video, or the like. For example, video interface 246 may be coupled to a digital video camera, a web-camera, or the like. Video interface 246 may comprise a lens, an image sensor, and other electronics. Image sensors may include a complementary metal-oxide-semiconductor (CMOS) integrated circuit, charge-coupled device (CCD), or any other integrated circuit for sensing light.

Client computer 200 also comprises input/output interface 248 for communicating with external devices, such as a headset, or other input or output devices not shown in FIG.

2. Input/output interface 248 can utilize one or more communication technologies, such as USB, infrared, Bluetooth™, or the like.

Haptic interface 250 is arranged to provide tactile feedback to a user of the client computer. For example, the haptic interface 250 may be employed to vibrate client computer 200 in a particular way when another user of a computer is calling. In some embodiments, haptic interface 250 may be optional.

Client computer 200 may also include GPS transceiver 232 to determine the physical coordinates of client computer 200 on the surface of the Earth. GPS transceiver 232, in some embodiments, may be optional. GPS transceiver 232 typically outputs a location as latitude and longitude values. However, GPS transceiver 232 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of client computer 200 on the surface of the Earth. It is understood that under different conditions, GPS transceiver 232 can determine a physical location within millimeters for client computer 200; and in other cases, the determined physical location may be less precise, such as within a meter or significantly greater distances. In one embodiment, however, client computer 200 may through other components, provide other information that may be employed to determine a physical location of the computer, including for example, a Media Access Control (MAC) address, IP address, or the like.

Mass memory 226 includes a Random Access Memory (RAM) 204, a Read-only Memory (ROM) 222, and other storage means. Mass memory 226 illustrates an example of computer readable storage media (devices) for storage of information such as computer readable instructions, data structures, program modules or other data. Mass memory 226 stores a basic input/output system (BIOS) 224, or the like, for controlling low-level operation of client computer 200. The mass memory also stores an operating system 206 for controlling the operation of client computer 200. It will be appreciated that this component may include a general-purpose operating system such as a version of UNIX, or LINUX™, or a specialized client communication operating system such as Microsoft Corporation's Windows Mobile™ Apple Corporation's iOS™, Google Corporation's Android™, or the like. The operating system may include, or interface with a Java virtual machine module that enables control of hardware components and/or operating system operations via Java application programs.

Mass memory 226 further includes one or more data storage 208, which can be utilized by client computer 200 to store, among other things, applications 214 and/or other data. For example, data storage 208 may also be employed to store information that describes various capabilities of client computer 200. The information may then be provided to another computer based on any of a variety of events, including being sent as part of a header during a communication, sent upon request, or the like. Data storage 208 may also be employed to store social networking information including address books, buddy lists, aliases, user profile information, user credentials, or the like. Further, data storage 208 may also store messages, web page content, or any of a variety of user generated content.

At least a portion of the information stored in data storage 208 may also be stored on another component of client computer 200, including, but not limited to processor readable storage media 230, a disk drive or other computer readable storage devices (not shown) within client computer 200. Further, at least a portion of data storage 208 may be used to store biometric profile information 210 for one or more users and/or one or more biometric devices.

Processor readable storage media 230 may include volatile, non-transitive, non-transitory, nonvolatile, removable, and non-removable media implemented in any method or technology for storage of information, such as computer- or processor-readable instructions, data structures, program modules, or other data. Examples of computer readable storage media include RAM, ROM, Electrically Erasable Programmable Read-only Memory (EEPROM), flash memory or other memory technology, Compact Disc Read-only Memory (CD-ROM), digital versatile disks (DVD) or other optical storage, magnetic cassettes, magnetic tape, magnetic disk storage or other magnetic storage devices, or any other physical medium which can be used to store the desired information and which can be accessed by a computer. Processor readable storage media 230 may also be referred to herein as computer readable storage media and/or computer readable storage device.

Applications 214 may include computer executable instructions which, when executed by client computer 200, transmit, receive, and/or otherwise process network data. Network data may include, but is not limited to, messages (e.g. SMS, Multimedia Message Service (MMS), instant message (IM), email, and/or other messages), audio, video, and enable telecommunication with another user of another client computer. Applications 214 may include, for example, a browser 218, and other applications 220. Further, applications 214 may include biometric authentication application 216, enrollment application 218, or the like.

Browser 218 may include virtually any application configured to receive and display graphics, text, multimedia, messages, and the like, employing virtually any web based language. In one embodiment, the browser application is enabled to employ HDML, WML, WMLScript, JavaScript, SGML, HTML, XML, and the like, to display and send a message. However, any of a variety of other web-based programming languages may be employed. In one embodiment, browser 218 may enable a user of client computer 200 to communicate with another network computer, such as biometric authentication service computer 116 as shown in FIG. 1.

Other applications 220 may include, but are not limited to, calendars, search programs, email clients, IM applications, SMS applications, voice over Internet Protocol (VOIP) applications, contact managers, task managers, transcoders, database programs, word processing programs, software development tools, security applications, spreadsheet programs, games, search programs, and so forth.

Illustrative Network Computer

Figure 3:
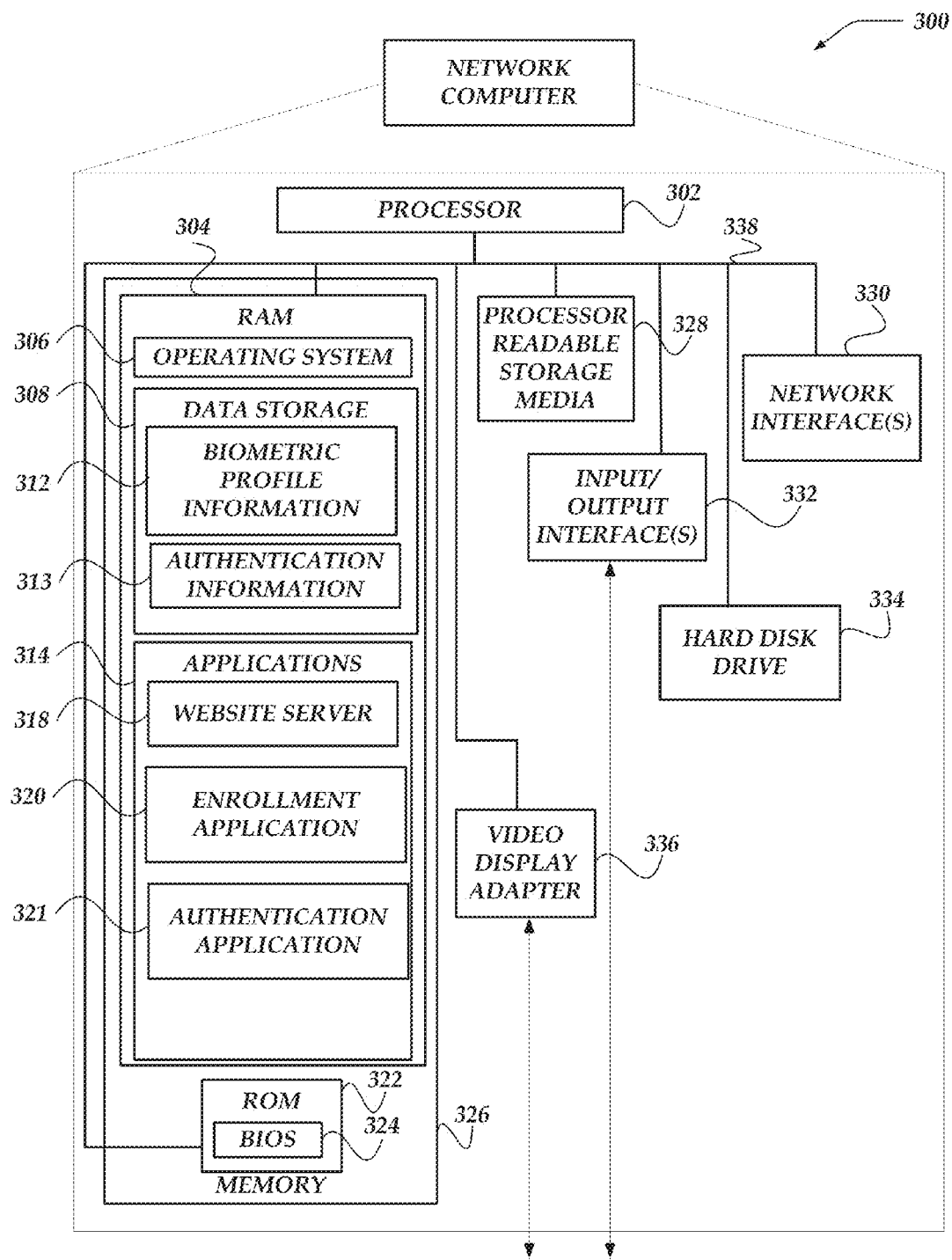
FIG. 3 shows one embodiment of a network computer, according to one embodiment of the invention.

FIG. 3 shows one embodiment of a network computer 300, according to one embodiment of the invention. Network computer 300 may include many more or less components than those shown. The components shown, however, are sufficient to disclose an illustrative embodiment for practicing the invention. Network computer 300 may be configured to operate as a server, client, peer, a host, cloud instance, or any other computer. Network computer 300 may represent, for example biometric authentication server computer 116, and/or other network computers.

Network computer 300 includes processor 302, processor readable storage media 328, network interface unit 330, an input/output interface 332, hard disk drive 334, video display adapter 336, and memory 326, all in communication with each other via bus 338. In some embodiments, processor 302 may include one or more central processing units.

As illustrated in FIG. 3, network computer 300 also can communicate with the Internet, or other communication networks, via network interface unit 330, which is constructed for use with various communication protocols including the TCP/IP protocol. Network interface unit 330 is sometimes known as a transceiver, transceiving device, or network interface card (NIC).

Network computer 300 also comprises input/output interface 332 for communicating with external devices, such as a keyboard, or other input or output devices not shown in FIG. 3. Input/output interface 332 can utilize one or more communication technologies, such as USB, infrared, NFC, Bluetooth, or the like.

Memory 326 generally includes RAM 304, ROM 322 and one or more permanent mass storage devices, such as hard disk drive 334, tape drive, optical drive, and/or floppy disk drive. Memory 326 stores operating system 306 for controlling the operation of network computer 300. Any general-purpose operating system may be employed. Basic input/output system (BIOS) 324 is also provided for controlling the low-level operation of network computer 300.

Although illustrated separately, memory 326 may include processor readable storage media 328. Processor readable storage media 328 may be referred to and/or include computer readable media, computer readable storage media, and/or processor readable storage device. Processor readable storage media 328 may include volatile, nonvolatile, non-transitory, non-transitive, removable, and non-removable media implemented in any method or technology for storage of information, such as computer readable instructions, data structures, program modules, or other data. Examples of processor readable storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other media which can be used to store the desired information and which can be accessed by a computer.

Memory 326 further includes one or more data storage 308, which can be utilized by network computer 300 to store, among other things, applications 314 and/or other data. For example, data storage 308 may also be employed to store information that describes various capabilities of network computer 300. The information may then be provided to another computer based on any of a variety of events, including being sent as part of a header during a communication, sent upon request, or the like. Data storage 308 may also be employed to store messages, web page content, or the like. At least a portion of the information may also be stored on another component of network computer 300, including, but not limited to processor readable storage media 328, hard disk drive 334, or other computer readable storage medias (not shown) within network computer 300.

Data storage 308 may include a database, text, spreadsheet, folder, file, or the like, that may be configured to maintain and store user account identifiers, user profiles, email addresses, IM addresses, and/or other network addresses; or the like. Data storage 308 may further include program code, data, algorithms, and the like, for use by a processor, such as processor 302 to execute and perform actions. In one embodiment, at least some of data store 308 might also be stored on another component of network computer 300, including, but not limited to processor-readable storage media 328, hard disk drive 334, or the like.

Data storage 308 may include biometric profile information 312. In at least one of the various embodiments, biometric profile information 312 may include information, such as, one or more files, that include biometric data for one or more users, or the like, used for authentications of wearable biometric devices. Also, in at least one of the various embodiments, data storage 308 may include, authentication information 313 that may include information about users, access points, access control lists, or the like.

Applications 314 may include computer executable instructions, which may be loaded into mass memory and run on operating system 306. Examples of application programs may include transcoders, schedulers, calendars, database programs, word processing programs, Hypertext Transfer Protocol (HTTP) programs, customizable user interface programs, IPSec applications, encryption programs, security programs, SMS message servers, IM message servers, email servers, account managers, and so forth. Applications 314 may also include, enrollment application 320 for enrolling and/or activating biometric devices. Application mat also include authentication application 321 for authenticating users by employ biometric information, biometric devices, additional conditions, or the like.

Website server 318 may represent any of a variety of information and services that are configured to provide content, including messages, over a network to another computer. Thus, website server 318 can include, for example, a web server, a File Transfer Protocol (FTP) server, a database server, a content server, email server, or the like. Website server 318 may provide the content including messages over the network using any of a variety of formats including, but not limited to WAP, HDML, WML, SGML, HTML, XML, Compact HTML (cHTML), Extensible HTML (xHTML), or the like.

Biometric Device

In at least one of the various embodiments, a wearable biometric device, such as, biometric device 106 may be any device that may be employed, typically, worn or held, by a user and is capable of obtaining a biometric signal. Non-limiting examples of wearable biometric devices are a wristband, wristwatch, bracelet, necklace, ring, belt, glasses, clothing, hat, headband or earring(s), or any other item that is capable of obtaining a biometric signal. The wearable biometric device can also be incorporated into clothing. In another embodiment, the wearable biometric device comprises more than one biometric sensor.

However, for at least one of the various embodiments, biometric devices within the scope of these innovations are not limited exclusively to wearable devices. In at least one of the various embodiments, biometric devices in non-wearable form factors may be considered to be within the scope of the innovations described herein. For example, a fixed biometric device embedded in a chair, desk, handle bar, or the like, or combination thereof. Likewise, biometric devices that may be held rather worn are also contemplated to be within the scope of the innovations described herein. However, in the interest of clarity and brevity most of the discussion and examples presented herein are described in terms of wearable biometric devices. One of ordinary skill in the art will appreciate the other biometric device form factors are within the scope of these innovations and are envisaged.

In at least one of the various embodiments, a user of a wearable biometric device may be authenticated with one or more biometric technologies or sensors that may capture biometric signals and/or data that represent biometric features that may be employed to uniquely identify the user.

The uniqueness of a biometric feature may be directly related to the underlying inter-individual differences in a population. Some non-limiting examples of biometric data that may be employed to uniquely identify a user are gait, heart rate, galvanic skin response, temperature, fingerprint, voice or voiceprint, body electrical characteristic, body thermal characteristic, iris pattern, vein pattern, eye vein pattern, facial or other anatomical structure, electrocardiogram, photoplethysmogram, electromyogram, electroencephalogram, transient otoacoustic emissions, phonocardiogram, DNA, one or more chemical markers, one or more biochemical markers, skin-color variation or discoloration, or perspiration. In addition, multi-modal biometric identification may be accomplished to increase accuracy and/or security. Various types of low power sensors for the acquisition of these biometric signals may be embedded in the wearable biometric device.

In at least one of the various embodiments, the wearable biometric device may include an onboard power source to enable the biometric device to perform the required functions, such as obtaining the biometric signal, transmitting and receiving the biometric and control signals, and maintaining a detector for detecting the removal of the wearable biometric device, such as an electronic continuity detector. Any power source known to the skilled person is acceptable, with non-limiting examples being battery, photovoltaic, kinetic, or microgenerator, thermal, piezo-electric generator, inductive charging, and wireless power transfer.

A wearable biometric device may include one or more radios/transceivers for transmitting and receiving communications with the authorized authentication device as well as systems installed at access points. The wearable biometric device may include one or more radios/transceivers for transmitting the biometric signal to the authorized authentication device such that the authorized authentication device may authorize the biometric signal. In this way, the wearable biometric device has the capability of transmitting and receiving information from the authorized authentication device in to authenticate users. In at least one of the various embodiments, the radios/transceivers for communicating with the AAD and for transmitting a control signal to an access point may use the same technology and/or protocols, or they may be different depending on the arrangement of the system.

In one example, the wearable biometric device may incorporate a wireless connectivity module such as Bluetooth 4.0 Low Energy (BLE), Near-Field Communications (NFC), WiFi, or other wireless technology capable of transmitting and receiving functions. In one embodiment, a BLE radio may be used because it may consume significantly less power when communicating in short bursts. In this way, a battery or other power source used to power the wearable biometric device may have an extended life, in some cases on the order of multiple weeks.

In at least one of the various embodiments, the radios and/or transceivers may be used to transmit biometric data during initialization and authentication, identify the user, and to establish a unique biometric profile associated with the user and the wearable biometric device. The same or other the radios and/or transceivers included in a wearable biometric device may also transmit and receive motion data and proximity data in order to be aware of local access points. In at least one of the various embodiments, the radios and/or transceivers may also be used to receive a positive authentication message that puts the wearable device into an authenticated state, as well as to prompt the user of notification events.

In at least one of the various embodiments, the wearable biometric device may be arranged to include proximity sensors for sensing an authorized authentication device or an access point. This may be a feature of the Bluetooth 4.0 standard which may be used by radios and/or transceivers included in the biometric device. Also, in at least one of the various embodiments, the wearable biometric device may be arranged to transmit a beacon signal along with the transmitting signal strength. Accordingly, the receiving device may use this information, along with the received signal strength, to estimate the proximity of the wearable biometric device. Non-limiting exemplary uses of the proximity data may include: only unlocking a device when the proximity is within a specified range, i.e., a door lock is only unlocked when the authorized user is within a certain distance, such as 50 cm; a "digital leash" which warns the user when a paired device is no longer within a certain proximity; or the like.

In at least one of the various embodiments, the wearable biometric device may utilize electrocardiogram (ECG) technology, such as, ECG biometric authentication for biometric authentication. In at least one of the various embodiments, ECG biometric authentication technology may use unique features of a user's electrocardiogram (ECG) to create a highly personalized biometric signature for that individual. Like other biometric characteristics, the ECG is universal, unique for every individual, and permanent over time. An ECG may be recorded for every living user, with no exclusion criteria. In addition, studies have shown that even though aspects of the ECG signal may get distorted with time and aging, the overall diacritical characteristics are observable. In the case of ECG, the uniqueness of the biometric feature is a result of several parameters of the cardiac function that control the waveforms. Electrophysiological variations of the myocardium such as the heart mass orientation and exact position, or the timing of depolarization and repolarization add to the idiosyncratic properties of every person's ECG waveforms.

In at least one of the various embodiments, one or more well-known ECG biometrics algorithms may analyze the overall pattern of the signal waveform rather than specific characteristics of the heart-beats and are therefore referred to as "fiducial-independent". One of the core algorithms is referred to as the AC/LDA (Autocorrelation/Linear Discriminant Analysis) and has become a standard for the comparison of fiducial dependent and independent algorithms.

Among the strengths of ECG in biometric recognition is its continuous property. Unlike static iris or fingerprint images that are scanned at a single point in time, the ECG signal has a continuous flow which can be used to continuously reassess the identity of a user. Furthermore, ECG biometrics may be difficult to attack with common skimming, replay or obfuscation methods. In the design of the wearable biometric device, by incorporating a two-lead ECG sensor with three electrodes, two adjacent electrodes on the underside of the wearable device (touching the skin of the user) and one on the top-side, a unique ECG signal can be obtained from the user. In one embodiment, the wearable device is a bracelet, cuff or watch, and the underside of the wearable device having the two adjacent electrodes makes contact with the wrist of the user. Alternatively, ECG data may be captured from both leads when the user touches the top-side electrode with the opposite hand. (See, FIG. 5) In at least one of the various embodiments, a single channel signal may be derived by combining the two signals to reduce noise. In other embodiments, analog and digital filters may be employed to reduce noise.

In at least one of the various embodiments, a number of mechanisms for initiation of ECG capture and authentication may be used. For example, the biometric device may be arranged to automatically sense when a top electrode is touched, such as using an embedded "lead on/off" detection system, optionally with notification of the lead status to the user. Further, the biometric device may be arranged to include a user input on the wearable biometric device, or on the Authorized Authentication Device (AAD) with a related application installed.

In at least one of the various embodiments, when ECG capture and authentication are initiated, the single-channel filtered ECG data may be transmitted to the AAD. The processes of enrollment and authentication are described below. Using a function within the application on the AAD, biometric enrollment may be initiated wherein the user touches the wearable biometric device and then ECG is captured and transmitted to the AAD. This process may take as little as about 1 second and up to a few seconds, a minute, or a few minutes depending on the level of interaction with the user with the wearable biometric device and the type of biometric signals being obtained.

In at least one of the various embodiments, the biometric profile may be created in a number of different ways. In one way, the biometric signal may be transmitted to a cloud service, where the processing is performed on the cloud servers to generate the biometric profile. Alternatively, the biometric signal may be processed on the AAD within an application to generate the biometric profile.

In at least one of the various embodiments, once the biometric profile is created, it may be associated with a user and stored within a cloud service. Also, in at least one of the various embodiments, the biometric profile may be transmitted to the Authorized Authentication device and stored locally. The biometric profile may be stored within a cloud service and authentication may be performed at the same location. In at least one of the various embodiments, the biometric profile may be stored on a wearable biometric device that is arranged to include the processing power required to authenticate the user. In another alternative, the processing for the creation of the biometric profile may be performed on the AAD or in the wearable biometric device itself.

In at least one of the various embodiments, the wearable biometric device may include one or more of: a CPU or system on a chip (SOC), which acts as the controller, a wireless transceiver, an antenna, and a user interface. The controller may be operative for controlling the overall operation of the wearable biometric device. The controller functionality may be implemented within, for example, one or more digital processing devices within the wearable biometric device. The wireless transceiver is operative for supporting wireless communication between the wearable biometric device and one or more other wireless entities including the AAD and wireless access points. In one embodiment, separate transceivers are provided within the wearable biometric device to support wireless communication between the wearable biometric device and other systems or devices. The wireless transceiver may also be coupled to one or more antennas to facilitate the transmission and reception of wireless signals. Any type of antenna (s) may be used including, for example, a dipole antenna, a patch antenna, a helical antenna, an antenna array, and/or others, including combinations of the above.

In at least one of the various embodiments, a user interface may be operative for providing an interface between a user and the wearable biometric device. The user interface of a biometric device may include structures such as, for example, a keyboard, a liquid crystal display (LCD), a speaker, a microphone, mouse, stylus, one or more physical or electronic buttons, and/or any other form of device or structure that enables a user to input information or commands to the wearable biometric device or receive information or a notification from the device.

In one embodiment, the controller may first determine if the wearable biometric device (and, therefore, the user) is within a predetermined distance or proximity to the AAD and/or an access point. In one example, if the wearable biometric device is within proximity of an access point and the wearable biometric device transmits a control signal to the access point indicating that the user has been authenticated, the receiver at the access point may automatically enable access to the user. If the wearable biometric device later goes outside the predetermined distance from the access point, the access point may be locked. In one example, if the access point is a security protected desktop computer and the preauthorized user wearing their preauthorized wearable biometric device temporarily leaves her desk to go to lunch, the computer will automatically lock so that no one else may use it in the user's absence. Similarly, if the access point is a smartphone and the smartphone is inadvertently left somewhere by the user, or is stolen, the smartphone will automatically lock up and thus be unusable by an unauthorized party in possession thereof. When the user wearing the preauthorized wearable biometric device again comes within a predetermined distance of the smartphone, the smartphone will simply be unlocked without having to repeat the automatic log in procedure, assuming that the wearable biometric device remains preauthorized.

In at least one of the various embodiments, the wearable biometric device, no matter which type of biometric is used for authentication, should be able to maintain contact with the user such that in the case that the wearable device is removed from the user, the wearable device will require re-initialization with the authorized authentication device prior to authorizing access control. The purpose of maintaining contact of the wearable biometric device with the user is to ensure that an authorized biometric device cannot be transferred to a different user without requiring reauthorization with the AAD. Accordingly, although skin or body contact is not required at all times while the wearable device is in its authenticated state, the wearable device should be on the user in such a way that removal of the wearable will put the wearable device back to its unauthenticated state. In the unauthenticated state, the wearable biometric device is not enabled to transmit a control signal to an access point. The security of the present invention depends on ensuring that removal of the wearable device from the user is reliably detected. Accordingly, the wearable biometric device may be arranged such that removal from the user's body may be easily detected.

In one preferred embodiment, the wearable device may comprise an adjustable and/or openable clasp to assist the user with putting on and removing the wearable device. Removal of the wearable device may be sensed by the wearable biometric device, for example, by opening the clasp, cutting the band, or generally severing an electrical conduit such as an electronic continuity detector. One exemplary electronic continuity detector that may be used to detect device removal comprises a simple circuit within the wearable device that runs around the entire wrist and is broken when the clasp is opened or the band is cut. Other types of device removal detection may be used, for example, including disruption in skin contact detection by way of conductivity, heat flux, galvanic skin response or motion, or periodic or continuous biometric signal detection. Yet other non-limiting examples of device removal detection embodiments include pulse detection, skin temperature detection, ambient temperature detection, blood flow detection, pressure detection, ambient light detection, electromagnetic field detection, respiration detection, heart rate detection, electrocardiogram detection, photoplethysmogram detection, electromyogram detection, electroencephalogram detection, near infra-red detection, skin-color detection, close magnetic contact detection, and mechanical switch detection.

In at least one of the various embodiments, other than the biometric sensor in the wearable biometric device, additional sensors may be incorporated into the device to obtain additional biometric or environmental readings. Some non-limiting examples of an additional sensor are motion sensor, proximity sensor, barometric sensor, pressure sensor, thermometer, microphone, near infrared sensor, light sensor, GPS sensor, capacitive sensor, gyroscope, manometer, camera, humidity sensor, hall sensor, galvanic skin sensor, photoplethysmogram sensor, electroencephalogram sensor, electromyogram sensor, blood flow sensor, bioimpedance sensor, otoacoustic emission sensor, optical sensor, altimeter sensor or UV light sensor. These additional sensors may provide one or more contextual signals such as the location of the wearable device and/or proximity to trusted environments.

In at least one of the various embodiments, a wearable biometric device may comprise one or more motion sensors that may be used for a variety of purposes, including but not limited to, user input (e.g., tap detection), activity tracking (e.g., pedometer, sports, fitness, etc.), gesture recognition, or the like. In one embodiment, a wearable biometric device may incorporate a six-axis motion sensor using an integrated accelerometer and gyroscope application-specific integrated circuit (ASIC). Embedded motion sensors may also be utilized for simple gesture recognition to indicate user intent, such as for example gestures may be used to distinguish between user intents to unlocking different locks on an automobile, such as, the driver door, passenger door, the trunk, or the like. In this way, computational requirements on the wearable biometric device may be kept at a minimum.

In at least one of the various embodiments, the wearable biometric device may be arranged to include notification devices and procedures to alert the user of one or more notification events. Some non-limiting examples of these include one or more notification LEDs and/or a vibration motor. A notification event may be an event detected by the wearable biometric device that the user should be aware of. These events may include: when the wearable device has been put into an authenticated state; when the wearable biometric device is communicating with other devices; when the wearable device is sensing motion; and/or when some event has occurred on a paired device, such as receiving an email or text. A paired device may be the AAD as well as any device system that interacts with the wearable biometric device.

In at least one of the various embodiments, the wearable device may also comprise other components such as a display screen, input devices (such as, for example, button, switch, keypad or touchscreen), timepiece/timers, tracking or global positioning (GPS) detector activity, or physiology or emotion tracking. In at least one of the various embodiments, biometric device may be arranged to indicate proximity to other devices. In at least one of the various embodiments, biometric devices may be arranged to include additional electronics for storing data for access and use not related to the presently described security system.

Figure 4A:
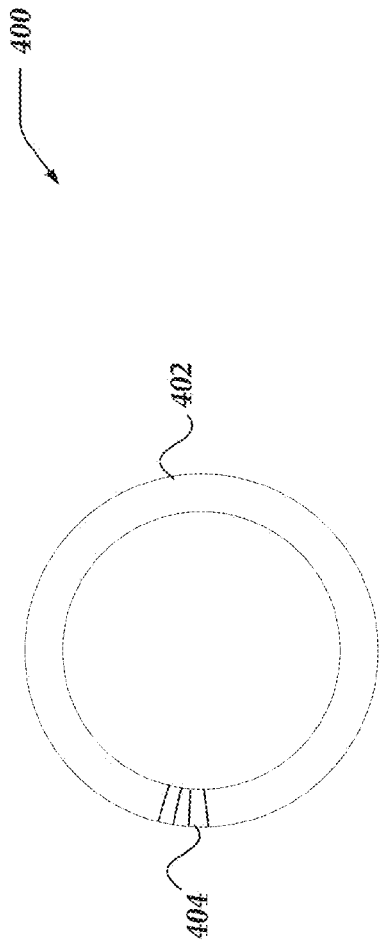
FIG. 4A and FIG. 4B illustrate a logical illustration of a wearable biometric device that is in accordance with at least one of the various embodiments.
Figure 4B:
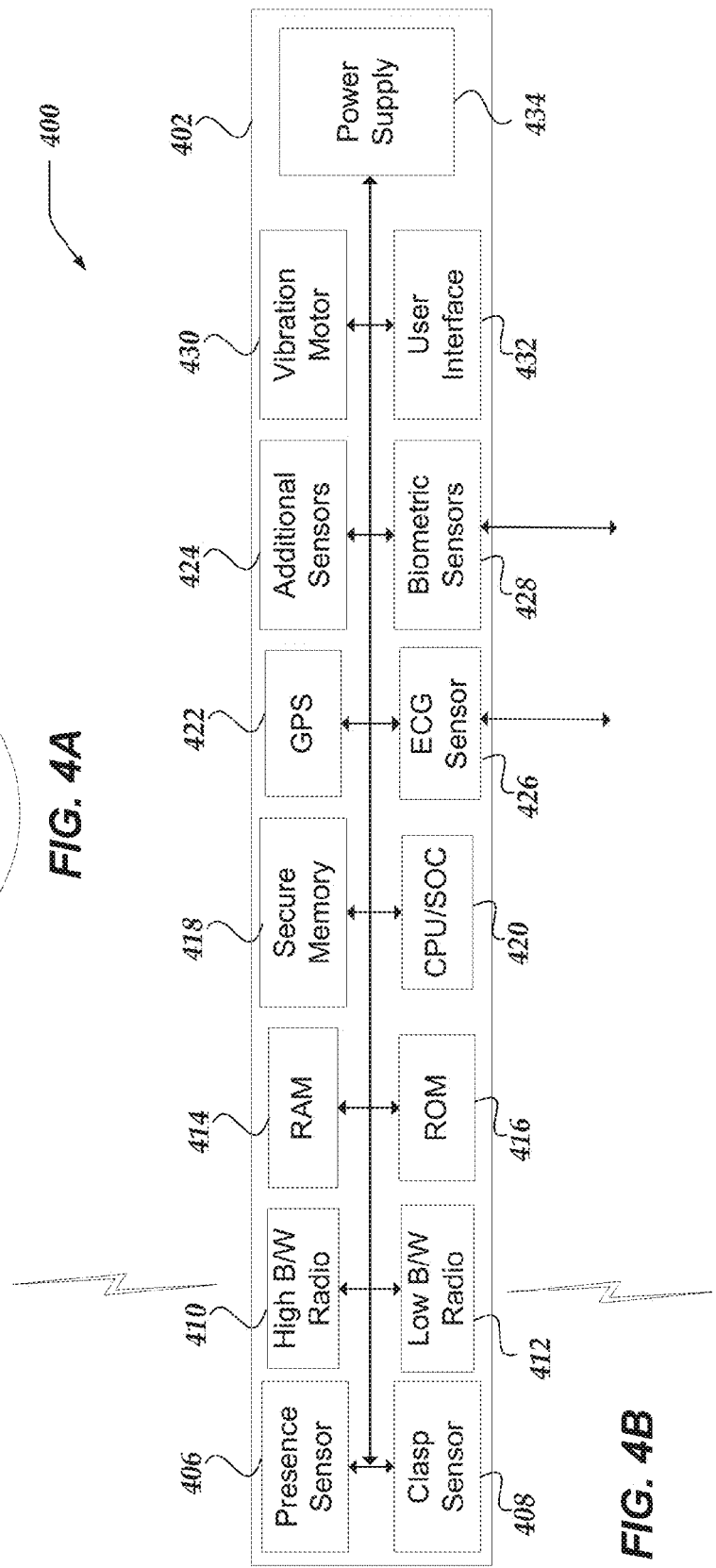

FIG. 4A and FIG. 4B illustrates a logical illustration of a wearable biometric device that is in accordance with at least one of the various embodiments.

FIG. 4A illustrates biometric device 400 that is arranged as a wearable wristband/bracelet. In at least one of the various embodiments, wristband 402 may be arranged to include various hardware components, sensors, and software for capturing biometric signals from its wearer; communication with an AAD or access point; authentication of a wearer, or the like, as discussed above. Further, in at least one of the various embodiments, wristband 402 may include an adjustable clasp mechanism, such as, clasp 404, for detecting if a wearable removes wristband 402 from his or her wrist. For example, in at least one of the various embodiments, if a biometric device detects that the clasp is opened, it may automatically de-authenticate itself.

FIG. 4B illustrates a logical view of some of the various components that may comprise a biometric device in accordance with at least one of the various embodiments. In at least one of the various embodiments, wristband 402 may include one or more presence sensors, such as, presence sensor 406, presence sensors may be arranged to determines if biometric device is in the presence of a wearer, AAD, access point, or the like, or combination thereof. Also, in at least one of the various embodiments, biometric device 402 may include one or more radios or transceivers, such as, high bandwidth radio 410 and low bandwidth radio 412. These radios may enable a biometric device to communicate with other computer or devices, such as, AADs' access points, biometric authentication servers, or the like, or combination thereof.

In at least one of the various embodiments, clasp sensor 408, may be arranged to determine if the clasp, or other securing mechanism, is opened or closes. In at least one of the various embodiments, an opened clasp may indicate that the biometric device may be separated from its authenticated user. Accordingly, for example, the biometric device may be arranged to automatically reset or otherwise de-authenticate itself if clasp sensor 408 indicates that the biometric device is removed from the wearer. Further, removal of the wearable device may be sensed by the biometric device for example, by opening the clasp, cutting the band, or generally severing an electrical conduit such as an electronic continuity detector. One exemplary electronic continuity detector that may be used to detect device removal comprises of a simple circuit within the wearable device that runs around the entire wrist and is broken when the clasp is opened or the band is cut. Other types of device removal detection may be used, for example, including disruption in skin contact detection by way of conductivity, heat flux, galvanic skin response or motion, or periodic or continuous biometric signal detection. Yet other non-limiting examples of device removal detection embodiments include pulse detection, skin temperature detection, ambient temperature detection, blood flow detection, pressure detection, ambient light detection, electromagnetic field detection, respiration detection, heart rate detection, electrocardiogram detection, photoplethysmogram detection, electromyogram detection, electroencephalogram detection, near infra-red detection, skin-color detection, close magnetic contact detection, and mechanical switch detection.

In at least one of the various embodiments, as discussed above, biometric device 402 may be arranged to communicate with various devices, such as, access points, AAD's, biometric servers and cloud services, or the like, or combination thereof. In at least one of the various embodiments, high bandwidth radio 410 may include radios for communication using high bandwidth mechanisms such as Wi-Fi, or the like. Low bandwidth radio 412 may represent components for communicating using low-power, shorter range radio systems such as, Blue Tooth, Blue Tooth Low Energy, NFC, RFID, or the like, or combination thereof. Further, in at least one of the various embodiments, these radios may be coupled to one or more antennas to facilitate the transmission and reception of wireless signals. Any type of antenna(s) may be used including, for example, a dipole antenna, a patch antenna, a helical antenna, an antenna array, and/or others, including combinations of the above.

In at least one of the various embodiments, RAM 414 may be non-volatile and/or volatile random access memory for storing information for operation of biometric device 402. In at least one of the various embodiments, all or portions of the contents of RAM 414 may be erased if the biometric device is removed of its wearer. Likewise, in at least one of the various embodiments, ROM 416 may contain data and/or instructions for the operation of the biometric device. In at least one of the various embodiments, ROM 416 may be "flashable," enabling it to be updated with system updates provided by an AAD or a biometric server service.

In at least one of the various embodiments, secure memory 418 may be a hardened tamper resistant memory device that is resistant to physical tampering. In at least one of the various embodiments, sensitive information such as cryptographic keys may be stored in secure memory 418.

In at least one of the various embodiments, biometric device 402 may be arranged to include CPU or System-on-a-Chip (SOC) for controller the operations of the biometric device. The performance capability go CPU/SOC 420 may vary depending on how much processing biometric device 402 is intended to perform.

In at least one of the various embodiments, GPS transceiver 422 may represent the radios, hardware, and instructions (e.g., software) for receiving geo-location. GPS transceiver 422 may determine the physical coordinates of biometric device 402 on the surface of the Earth. GPS transceiver 422 typically outputs a location as latitude and longitude values. However, GPS transceiver 422 may also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of biometric device 402 on the surface of the Earth. It is understood that under different conditions, GPS transceiver 422 may determine a physical location within millimeters for biometric device 402; and in other cases, the determined physical location may be less precise, such as within a meter or significantly greater distances.

In at least one of the various embodiments, additional sensors 424 represent one or more sensor systems including, additional sensors such as accelerometers, motion sensors, proximity sensors, barometric sensors, pressure sensors, thermometers, microphones, near infrared sensors, light sensors, capacitive sensors, gyroscopes, manometers, cameras, humidity sensors, hall sensors, galvanic skin sensors, photoplethysmogram sensors, electroencephalogram sensors, electromyogram sensors, blood flow sensors, bioimpedance sensors, otoacoustic emission sensors, optical sensors, altimeter sensors, UV light sensors, or the like.

In at least one of the various embodiments, as discussed above, biometric device 402 may be arranged to include a variety of biometric sensors for detecting, sensing, and/or sampling a variety of biometric signals from the wearer. ECG sensor 426 represents one or more sensors for detecting, sensing, and/or sampling ECG information as described above. Likewise, biometric sensors 428 represent one or more sensors for detecting, sensing, and/or sampling other biometric information as described above.

In at least one of the various embodiments, biometric sensor 402 may be arranged to include a variety of components for interacting with the wearer. Vibration motor 430 may enable the biometric device to vibrate to notify the wearer of various changes in state, or the like (as discussed above). Likewise, user interface 432 may comprise elements that enable a user to provide input to the biometric device or for receiving output from the biometric device as discussed above, including biometric data that may be employed to uniquely identify a user, such as, gait, heart rate, galvanic skin response, temperature, fingerprint, voice or voiceprint, body electrical characteristic, body thermal characteristic, iris pattern, vein pattern, eye vein pattern, facial or other anatomical structure, electrocardiogram, photoplethysmogram, electromyogram, electroencephalogram, transient otoacoustic emissions, phonocardiogram, DNA, one or more chemical markers, one or more biochemical markers, skin-color variation or discolouration, perspiration, or the like. Also, in at least one of the various embodiments, user interface 432 may include a key pad, buttons, LED's microphone (for voice commands), or the like, or combination thereof.

Also, in at least one of the various embodiments, power source 434 may be arranged to provide power of operating biometric device 402. Power source 434 may include various batteries, storage cells, power adapters, chargers, or the like, as well as, power sources such as, photovoltaic, kinetic, or microgenerator, thermal, piezo-electric generator, inductive charging, and wireless power transfer or the like, or combination thereof.

One or ordinary skill in the art will appreciate that biometric device 402 is a non-limiting example or a biometric device that is in accordance at least one of the various embodiments. Even though biometric device 402 represents a wristband wearable biometric device, biometric devices within the scope of these innovations may be arranged in other form factors, such as those discussed above.

Further, in at least one of the various embodiments, some or all of components described in FIG. 4B and/or elsewhere in this paper may be implemented in hardware, including, dedicated (custom) hardware, ASICs, FPGAs, or the like. Likewise, these components or portions thereof may be implemented in whole or in part using software.

For example, in at least one of the various embodiments, a wearable device may be arranged to omit features and components related to biometric sensors, biometric signals, or the like. In such embodiments, the preauthorization and/or authentication of the device may be based on non-biometric security factors. However, in the interest of brevity, the term biometric device is used throughout this description even though some wearable devices may be arranged to omit biometric features for authentication and/or preauthorization.

Figure 5:
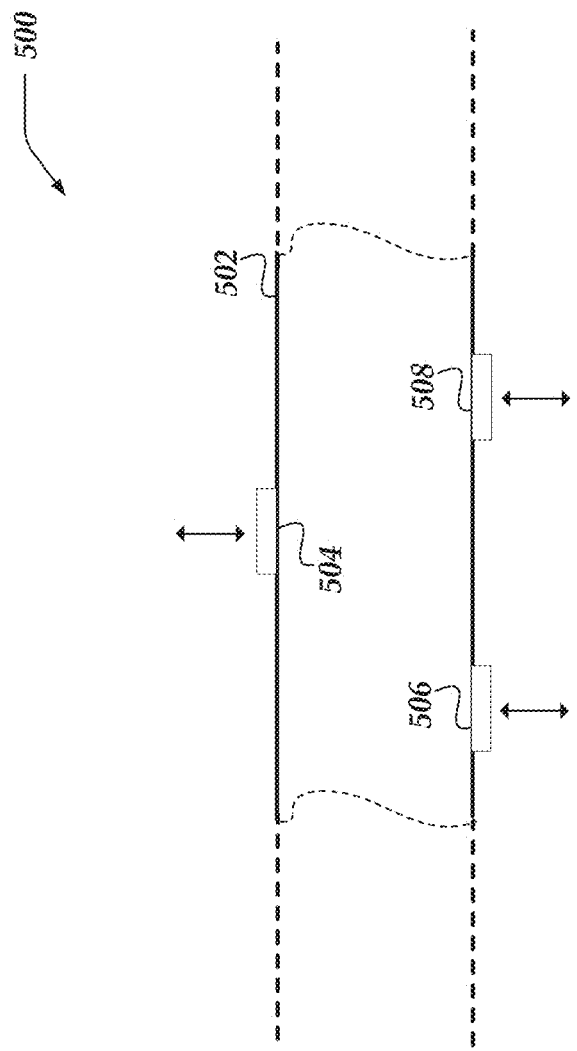
FIG. 5 illustrates a logical schematic of a biometric device showing sensors for electrocardiogram signal capturing in accordance with at least one of the various embodiments.

FIG. 5 illustrates a logical schematic of biometric device 500 showing sensors for ECG signal capturing in accordance with at least one of the various embodiments. In at least one of the various embodiments, biometric device section 502 represents a side cross-sections that highlights sensors one arrangement for capturing ECG signals. In at least one of the various embodiments, sensor 504, sensor 506, and sensor 508, represents sensor contacts (e.g., electrodes) arranged to capture ECG signals upon direct contact of a user's skin. In at least one of the various embodiments, sensor 506 and sensor 508 are arranged to contact the skin of the user's wrist that is wearing the biometric device. Sensor 504 is arranged to enable the user to touch with a finger of his or her opposite hand (the hand not wearing the biometric device). Accordingly, a circuit may be made from one hand to the other, enabling ECG signals to be captured through the sensors. Note, one of ordinary skill in the art will appreciate that other sensor arrangements may be employed. Further, more or fewer sensors may be arranged in different positions—however, the arrangement disclosed in FIG. 5 is at least sufficient for practicing the innovations described herein.

Generalized Operation

FIGS. 6-15 represent the generalized operations of generating application that may include generic function in accordance with at least one of the various embodiments. In at least one of the various embodiments, processes 600, 700, 800, 900, 1000, 1100, 1200, 1300, 1400, and 1500 described in conjunction with FIGS. 6-15 or portions thereof may be implemented by and/or executed on a single computer or device, such as client computer 200 of FIG. 2, network computer 300, biometric device 402, or the like. In other embodiments, these processes or portions of process thereof may be implemented by and/or executed on a plurality of network computers, such as network computer 300 of FIG. 3 or in a cloud/cloud service environment. Further, in at least one of the various embodiments, the processes described in conjunction with FIGS. 6-15 may be operative in biometric devices such as those described above and at least on biometric devices as described in conjunction with FIG. 4A, FIG. 4B, and FIG. 5.

Figure 6:
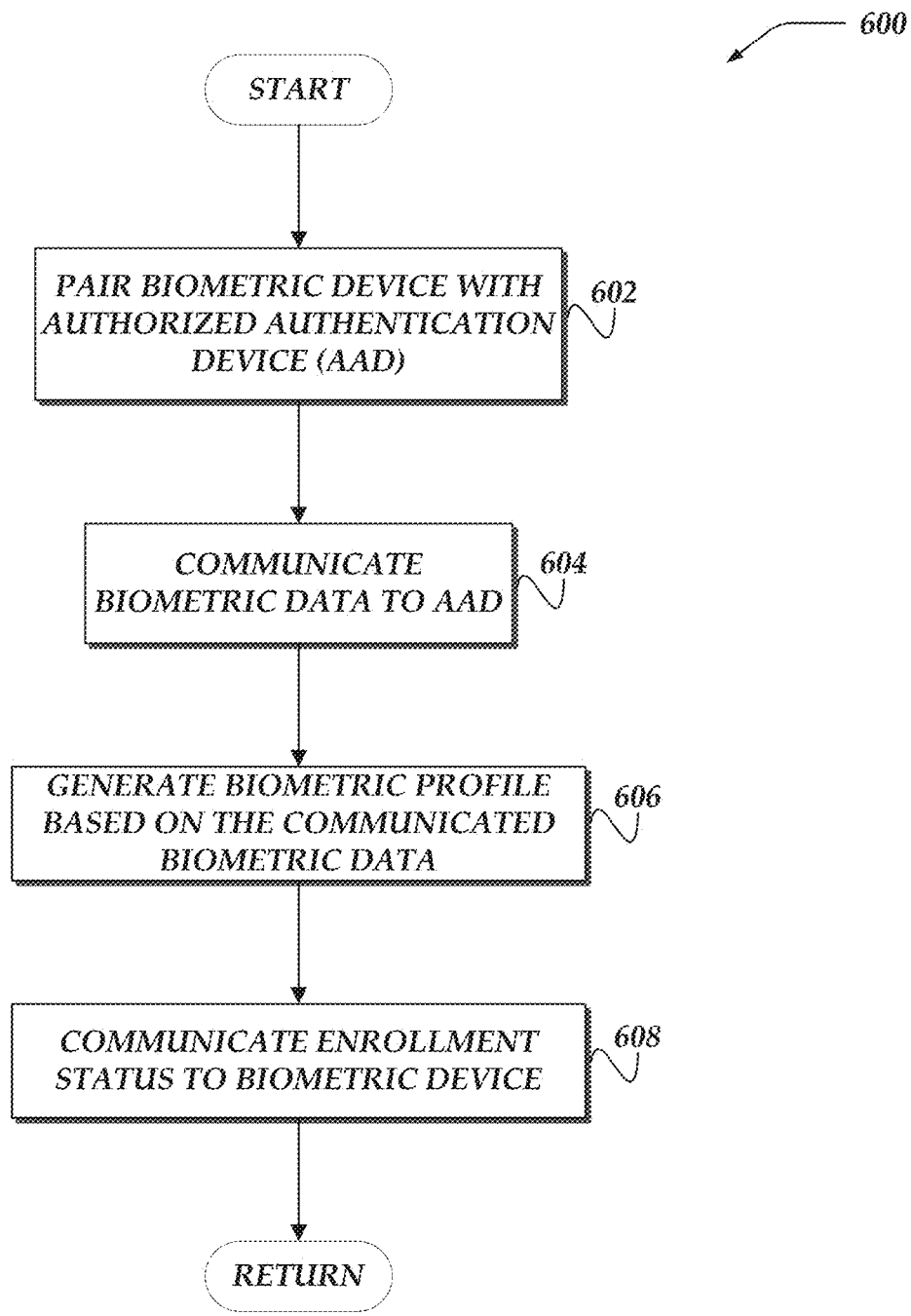
FIG. 6 shows an overview flowchart for a process for enrolling a biometric device in accordance with at least one of the various embodiments.

FIG. 6 shows an overview flowchart for process 600 for enrolling a biometric device in accordance with at least one of the various embodiments. In at least one of the various embodiments, enrollment or initialization of the user is performed when the user first uses the wearable biometric device. After a start block, at block 602, in at least one of the various embodiments, a biometric device may be paired with an authorized authentication device (ADD). In at least one of the various embodiments, the initial pairing operation may employ one features of the radio/sensing components included in the biometric device and the AAD. For example, BLE, NFC, Wifi, or the like.

In at least one of the various embodiments, the particular steps employed for pairing the biometric device with the AAD may vary depending on the underlying technology employed by the biometric device and the AAD for sensing and communicating. For example, well-known methods for Bluetooth pairing may be employed.

In at least one of the various embodiments, the AAD may be, for example, a smartphone, tablet, desktop computer, laptop computer, a terminal or network connected personal device. In one embodiment, an application may be installed on the AAD to facilitate communication between the AAD and the wearable biometric device. The AAD may be a personal device that has a pre-installed software application that the user has created an account with. The biometric profile of the user may be stored within this application. Since the AAD and the installed software are controlled by the user, the AAD constitutes a third factor of authentication in the present system. It also makes it possible to reduce the processing requirements on the wearable device, which may in return have lower power requirements.

At block 604, in at least one of the various embodiments, the biometric device may communicate one or more biometric signals and/or biometric data to the AAD. As discussed above the biometric device may be arranged to capture signals that represent one or more biometric features of the user.

At block 606, in at least one of the various embodiments, a biometric profile may be generated based on the biometric signals and/or biometric data provided by the biometric device. In at least one of the various embodiments, a biometric profile may include information that represents identifiable features of one or more biometric signals from a user. In at least one of the various embodiments, a user's biometric profile may be associated with one or more biometric measurements as described above.

In at least one of the various embodiments, additional information such as passwords, pass phrases, PIN's or the like, may be included in a user's biometric profile. In at least one of the various embodiments, the AAD application may enable a user to associate these additional security factors with their biometric profile.

In at least one of the various embodiments, the AAD may present one or more user interfaces to a user to collect user profile information (e.g., name, email address, or the like) that may be associated with the biometric profile.

At block 608, in at least one of the various embodiments, enrollment status may be communicated from the AAD to the biometric device. In at least one of the various embodiments, if the biometric device may be successfully enrolled a communication of this status may be communicated to the biometric device. Next, control may be returned to a calling process.

In at least one of the various embodiments, additional authentication factors may be employed during enrollment for high security applications. An optional motion sensor in the wearable device may enable, for example, recognition of secret hand gestures. Passwords, PINs, voice commands, finger tapping, finger swiping, or other deterministic user inputs may be used as additional authentication mechanisms. Once authenticated, the wearable device may be consider preauthorized and may stay in the preauthorized mode until it is separated from the user. In at least one of the various embodiments, the AAD application that is performing the enrollment actions may be configured to collect the additional authentication factors.

In at least one of the various embodiments, a biometric device may be arranged to be authenticated and/or enrolled with an AAD based on security factors that do include biometric information or features of the user. In such embodiments, the additional authentication factors described above may be employed for authenticating the biometric device absent biometric factors.

Figure 7:
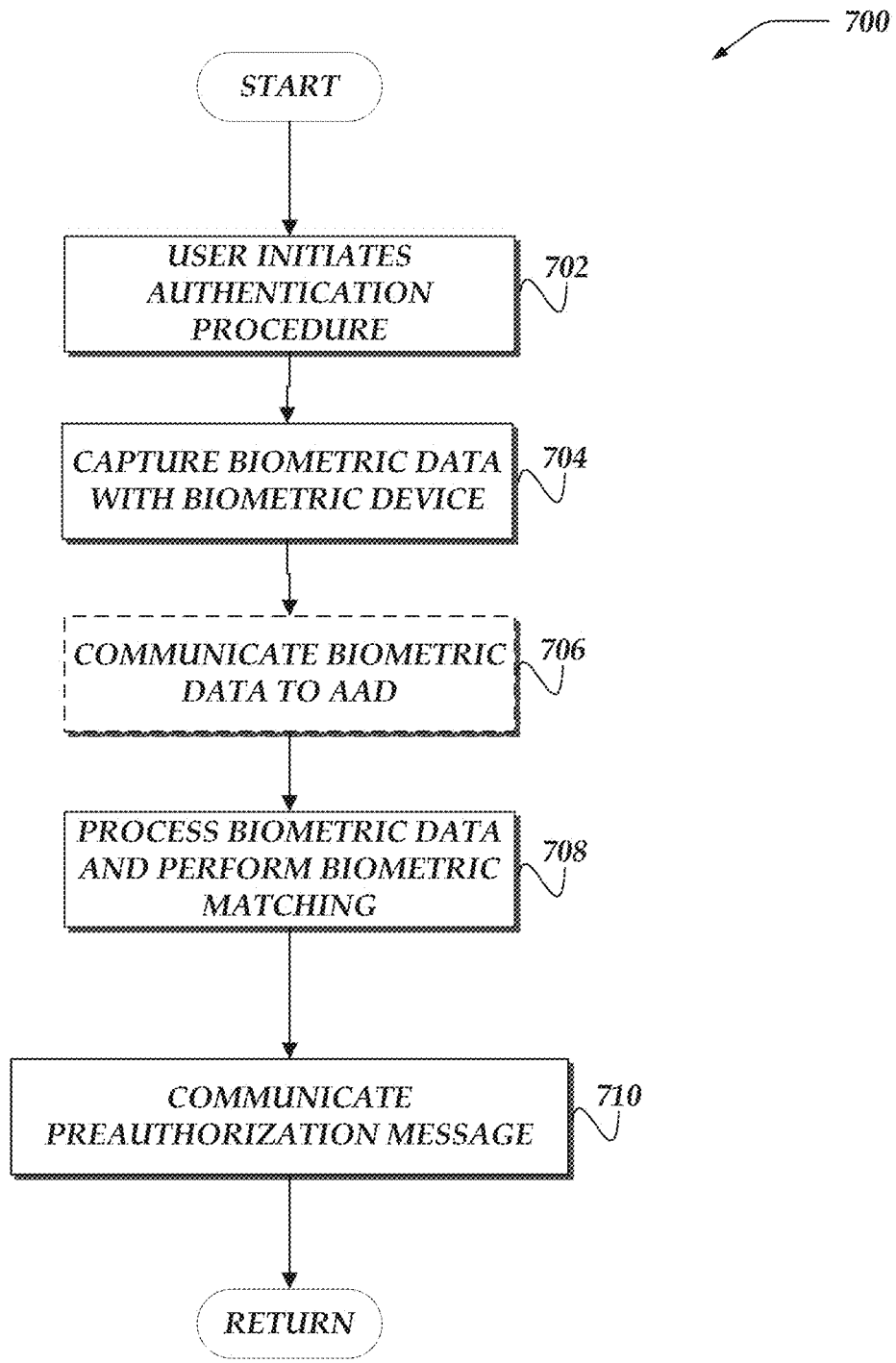
FIG. 7 shows an overview flowchart for a process for authenticating a biometric device with a previously enrolled user in accordance with at least one of the various embodiments.

FIG. 7 shows an overview flowchart for process 700 for preauthorizing a biometric device with a previously enrolled user in accordance with at least one of the various embodiments. After a start block, at block 702, in at least one of the various embodiments, a user may initiate a procedure for preauthorizing a biometric device.

At block 704, in at least one of the various embodiments, biometric data may be captured using the biometric device. A biometric signal of one or more biometric features of the user may be captured by the wearable device.

At block 706, in at least one of the various embodiments, optionally, the captured biometric data representing the captured biometric features of the user may be transmitted wirelessly to a paired AAD. In at least one of the various embodiments, this step may be optional because in some embodiments, the biometric data may be held on the biometric device rather than being communicated to the AAD.

At block 708, in at least one of the various embodiments, the biometric data may be processed and compared with one or more biometric profiles for correlating the biometric data to a user. In at least one of the various embodiments, to preauthorize the wearable biometric device subsequent to initialization, biometric data is received from the wearable biometric device and is authenticated on the biometric device or in some embodiments on the authorized authentication device. In either case, the biometric data may be authenticated based on a biometric profile that may be stored on the biometric or in some embodiments, on the AAD. In at least one of the various embodiments, the biometric signal obtained is then compared to the previously obtained biometric profile to perform a biometric matching.

At block 710, in at least one of the various embodiments, the authentication status based in part on the result of matching the biometric signal, may be communicated from the AAD to the biometric device. Alternatively, in at least one of the various embodiments, an authorization key may be generated on the biometric device and communicated to the AAD. In at least one of the various embodiments, the authorization key may be used by the AAD to decrypt user profile information that may correlate the user with the biometric device. Accordingly, the AAD may authenticate the user absent directly receiving biometric signals or biometric data.

Accordingly, in at least one of the various embodiments, if the biometric signal matches the user's biometric profile, the biometric device may be set into a pre-authorized state. In at least one of the various embodiments, the AAD may communicate a control signal to the biometric device signalling that biometric device should enter the pre-authorized state. Or, in at least one of the various embodiments, the authorization key provided by the biometric device may enable the AAD to decrypt the biometric profile of the user enabling the AAD to preauthorize the biometric device.

In at least one of the various embodiments, at this point the biometric device is authenticated as being worn by the user that corresponds to the matched biometric profile and is preauthorized for enabling access to one or more access points. Next, control may be returned to a calling process.

In at least one of the various embodiments, once successful authentication is achieved, the application on the AAD communicates back to the wearable device and preauthorizes it for the user. The biometric device remains in a preauthorized state until it is removed from the user or separated from the user.

In some embodiments, the preauthorization of the wearable biometric device may be performed twice per day, once per day, or even less frequently, such as every two days, every three days, every four days, every five days, every six days, or once per week.

Also, in at least one of the various embodiments, once the biometric device is preauthorized, the AAD does not need to be within wireless range of the wearable biometric device to enable the user to transmit a control signal to an access point in order to obtain access to a physical or logical access point. Further interaction between the wearable and the AAD is not required to obtain access to access points.

In at least one of the various embodiments, the wearable biometric device may further be trusted to remain associated with the same person during later transactions by detecting device removal from the user. In this way, the wearable device is able to transmit an authenticated control signal that serves as a proxy for user identity authentication. In essence, the wearable biometric device becomes a trusted arbiter or proxy of identity for every other device, access point and system that the user interacts with. Although the wearable biometric device is able to transmit a biometric signal as the control signal at an access point, the biometric preauthorization of the wearable device via the AAD enables the control signal to be other than a biometric signal.

In at least one of the various embodiments, biometric devices may be arranged to employ additional non-biometric security factors for preauthorizing an enrolled device, such as, gestures, passwords, PINs, voice commands, finger tapping, finger swiping, or other deterministic user inputs may be used as additional authentication mechanisms. In some embodiments, non-biometric security factors may be relied on absent biometric information.

Figure 8:
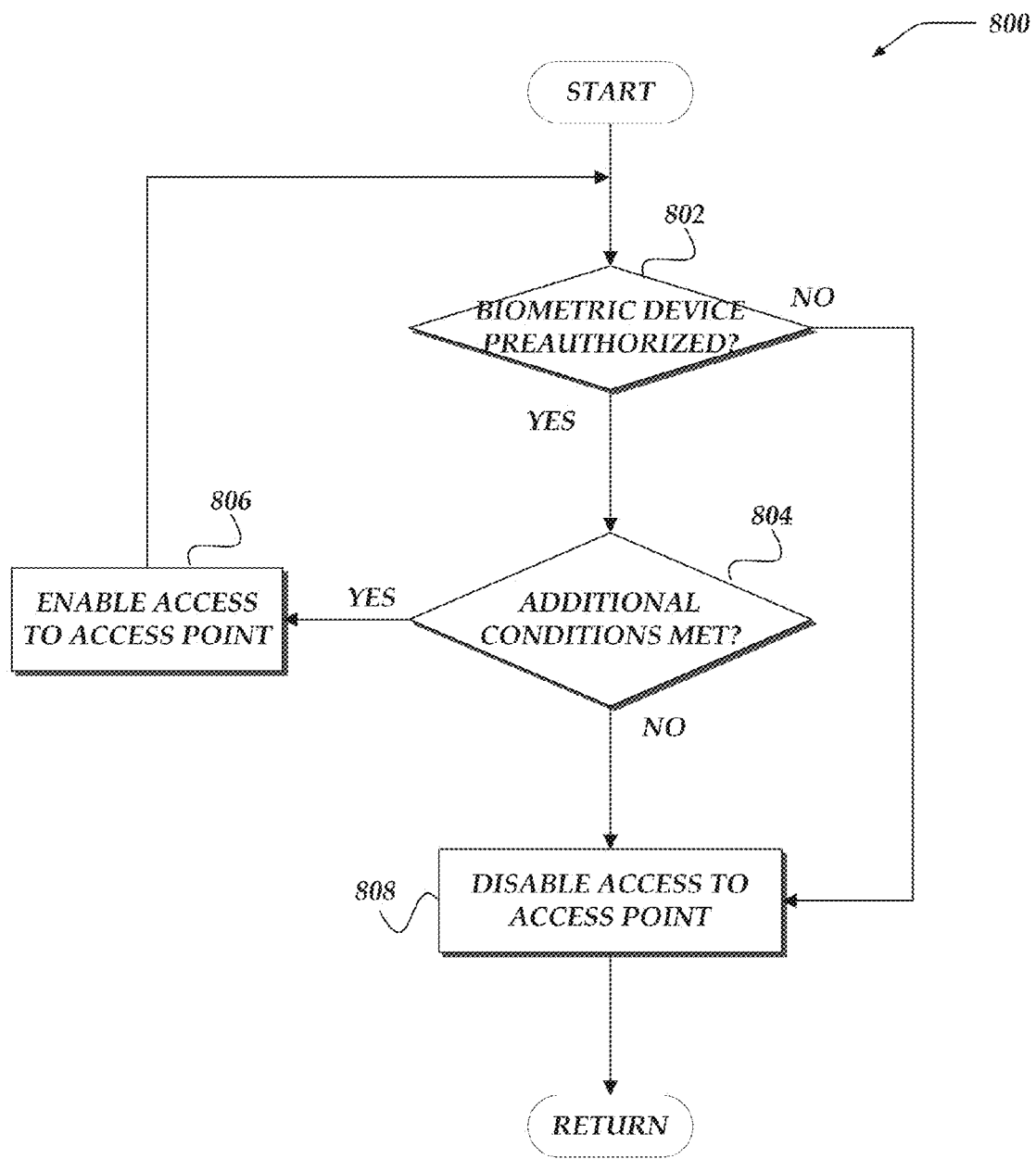
FIG. 8 shows an overview flowchart for a process for authenticating a user with one or more access points in accordance with at least one of the various embodiments.

FIG. 8 shows an overview flowchart for process 800 for authenticating a user with one or more access points in accordance with at least one of the various embodiments. After a start block, at decision block 802, in at least one of the various embodiments, if a preauthorized biometric device in range of an access point, control may flow block 804; otherwise control may flow to block 808.

At decision block 804, in at least one of the various embodiments, if one or more additional conditions (if any) are met, control may flow to block 806; otherwise control may flow to block 808. As discuss below, the biometric device, or the access point may be configured to require additional information before enabling access to the access point. In at least one of the various embodiments, additional security factors may be required to increase security, such as requiring one or more additional biometric features to authenticate the user, or requiring a password to be entered into the authorized authentication device. Such a password may be alphanumeric, or may be gestural or postural (finger tapping/swiping), captured by the wearable biometric device by the one or more sensors on the wearable device. Such additional security factors may be added to systems with high security requirements.

Also, in at least one of the various embodiments, additional conditions may be required based on information included in the user's profile. For example, the user profile may be configured to limit access to certain times of day or a certain number of times per day, and so on. See, FIG. 14 for a more detailed explanation of user profiles and their configuration.

Further, in at least one of the various embodiments, additional conditions may be required based on information included in the access point's profile. For example, the access profile may be configured to limit the number of preauthorized users that may obtain access to the access point each day, and so on. See, FIG. 15 for a more detailed explanation of access profiles and their configuration. Further, in at least one of the various embodiments, a condition may be membership of the user into one or more associations or groups, such as, employees, customers, VIP's, security, or the like, or combination thereof.

Also, in at least one of the various embodiments, the biometric device may include keys or other identifiers that may be associated with one or more groups or associations that may have issued the biometric device to the user. Accordingly, to meet the access conditions the biometric device may need to be authenticated and preauthorized as well as including the additional information indicating the biometric device associated with the correct group.

Moreover, in at least one of the various embodiments, an additional condition may be the requirement for one or more particular users to be sensed and authorized by the access point in addition the users attempting to obtain access. For example, one or more access points may be disabled from allowing any user access unless an authenticated supervisor user is sensed by the access point. In this example, an access point profile may be configured to disable other users unless a supervisor user is simultaneously sensed by the access point. Or, in at least one of the various embodiments, an access point may be configured to always require a certain number of authenticated users (e.g., 2, 3, 5) to be present and preauthorized before allowing any user to obtain access. For example, an access point configured to require two users to be present may be incorporated into an industrial machine that requires two authenticated operators for safety and/or security reasons.

At block 806, in at least one of the various embodiments, access to one or more access points may be enabled for the user that has the biometric device. Next, control may loop back to decision block 802. At block 808, in at least one of the various embodiments, access to one or more access points may be disabled. Next, control may be returned to a calling process.

In at least one of the various embodiments, user access to physical and logical access points may be controlled by a transmission of a control signal from the wearable biometric device to the access point. For example, in at least one of the various embodiments, one method of gaining entry at an access point may be to determine whether a wearable biometric device has been preauthorized and if that wearable biometric device is within an allowable range of the access point. If the answer is affirmative for both authorization and range to access point, the wearable biometric device may be arranged to transmit a control signal to the access point that affirmatively confirms that the biometric device is preauthorized. Accordingly, the user may obtain access to the access point. Further, authorization for access to an access point may be enabled by the wearable device at multiple access points subsequent to a single authorization by the AAD.

For example, in at least one of the various embodiments, user may access various access points through the course of a day with a single biometric authentication/preauthorization, such as, security doors at home, security doors at work, point-of-sale devices (e.g., to purchase coffee), wireless password entry to a personal electronic devices, gym or change-room security doors, transit payments, or the like. Accordingly, multiple secure transactions which traditionally have each required a unique security card or proof of identity may each be accessed using the same preauthorized biometric device employing a control signal affirmatively confirming that the biometric device is preauthorized.

In at least one of the various embodiments, if the wearable biometric device is in an authenticated mode, it may communicate this status information by wirelessly transmitting the control signals to devices and systems, such as, access points, that may be in the user's environment. Therefore, the presence of the user with the preauthorized biometric device within the range of a smart-connected access point device may be sufficient for unlocking and/or enabling access to the device. One method of determining proximity to access points is via measuring Bluetooth energy levels.

In at least one of the various embodiments, a preauthorized wearable biometric device may then be used to access/unlock the wearer's smartphone, tablet, online accounts, vehicle, and physical spaces, as well as provide personalization for smart environments, and allow third parties to detect their presence (e.g., office, club, retail environments, or the like).

In at least one of the various embodiments, another example of a logical access point is a paired device, which may include but is not limited to the authorized authentication device. For example, if a wearable biometric device has been preauthorized, other paired devices such as smartphones, computer terminals, tablets, laptops, environmental control systems which do not have the capability to authorize the wearable biometric device, but which would be otherwise locked, may be accessed via a control signal transmitted by the preauthorized wearable biometric device.

In at least one of the various embodiments, transmission of entry authorization signals from the preauthorized wearable biometric device to the desired access point by way of the control signal is preferably accomplished wirelessly. Some non-limiting examples of wireless technologies that may be used are Bluetooth, WIFI, NFC, or the like. In some embodiments, a wearable biometric device may be arranged to include more than one type of transmitter or transmitting means to accommodate the range of receivers that may be used at various access points. Additionally, in some embodiments, the wearable biometric device may be arranged to include more than one type of receiver or receiving technology. In this way, access points already in place may be accessed by incorporating the corresponding communication technology into the wearable biometric device.

In at least one of the various embodiments, if a person is wearing a preauthorized wearable biometric device, they may subsequently access devices and accounts in their environment that configured as access point (e.g., they include access point applications for controlling access). In the preferred embodiment a device or system acts as an access point that grants access to the user when the preauthorized wearable biometric device is detected to be in close proximity and when an authenticating control signal is received. In addition, access control may be further conditioned by requiring one or more of a determination of proximity/range of the wearable biometric device to the access point, the detection of a gestural input by the wearable biometric device, and additional skin or body contact detection by the wearable biometric device such as with a finger (tapping), password, PIN's voice commands, or the like, or combination thereof.

In a different embodiment a user may indicate an intent to access an access point using gesture control. Accordingly, in at least one of the various embodiments, the biometric device may be arranged for collecting, processing and matching motion or gestural signals to pre-defined or user-defined gestures. In one example, if an "unlock" gesture is performed by the user and detected by the authenticated wearable biometric device, an "access" control signal may be transmitted to the device or system comprising the access point that the user intends to access.

In at least one of the various embodiments, a user may indicate intent to access a device or system comprising an access point by touching or tapping the wearable biometric device with a body part, and/or making skin contact with the device. For example, to access a smartphone, the wearable biometric device may transmit a control signal to the smartphone indicating that the wearable biometric device is preauthorized, and is also within proximity to the device or system to be unlocked or accessed. Following that, the smartphone may be unlocked when user double taps the biometric device.

In another example, user intent with skin contact may be detected with a signal that is transmitted from the wearable biometric device to the access point that the user desires access through the human body. In at least one of the various embodiments, the wearable biometric device may be arranged to include a transmitter of a unique sequence and the accessing device is equipped with a receiver. Capacitive or galvanic coupling may be employed for the transmission of the signal through the body.

In at least one of the various embodiments, an adversary that intends to fraudulently put another person's device into the preauthorized/authenticated mode must first gain possession of the wearable biometric device as well as the authorized authentication device. Even if these two devices may be brought together, the adversary must still replicate or spoof the biometric signal of the initialized user.

Figure 9:
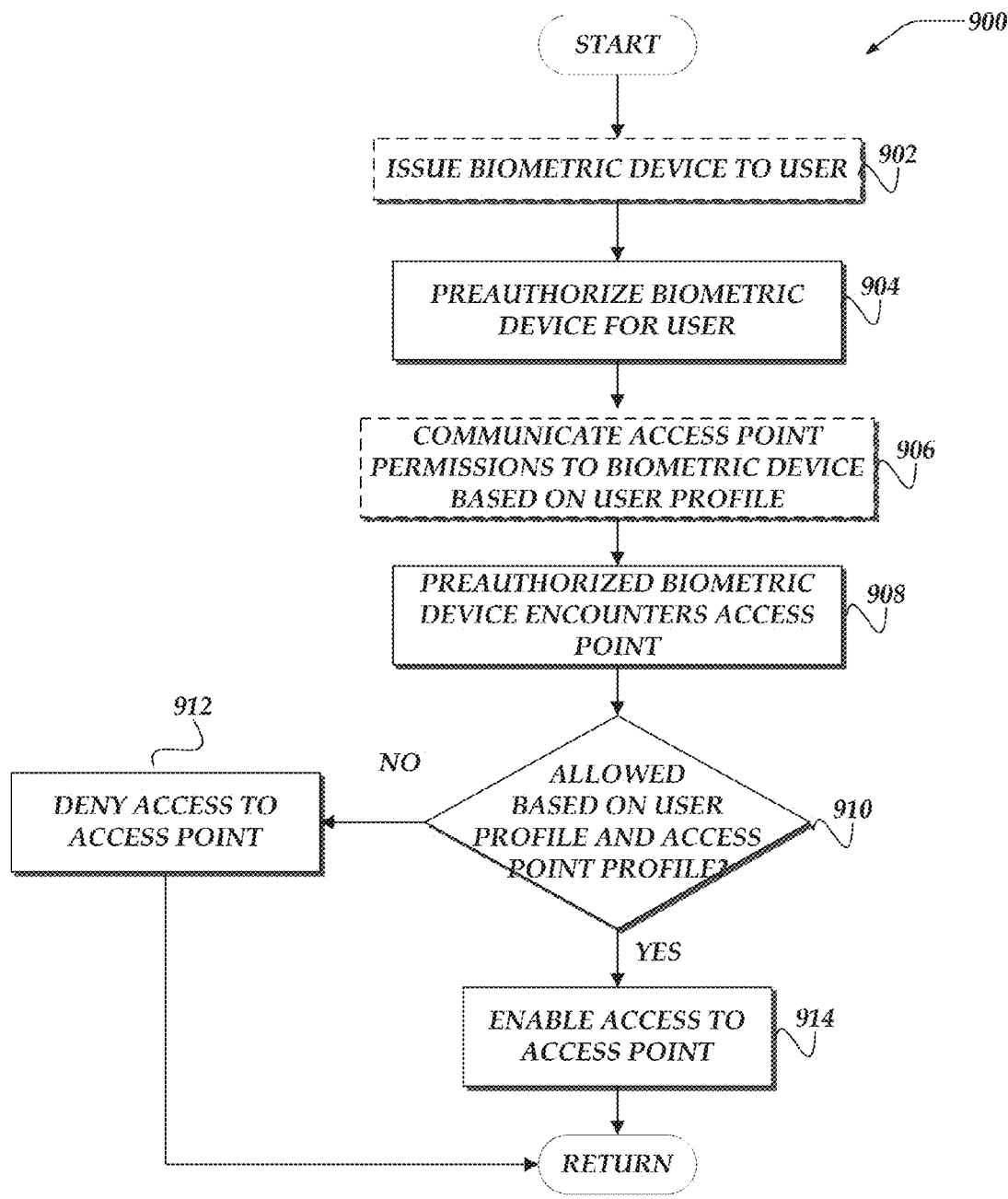
FIG. 9 shows an overview flowchart for a process for authenticating a user with one or more access points in accordance with at least one of the various embodiments.

FIG. 9 shows an overview flowchart for process 900 for authenticating a user with one or more access points in accordance with at least one of the various embodiments. After a start block, at block 902, in at least one of the various embodiments, optionally, a biometric device may be issued to a user. In at least one of the various embodiments, an organization, such as, an employer, school, entertainment provide, amusement park, or the like, may provide biometric devices to users that may be associated with the organization. In other cases, user may have their own biometric device.

At block 904, in at least one of the various embodiments, a biometric device may be authenticated for a particular user. Also, in at least one of the various embodiments, as discussed above, a biometric device may be enrolled and preauthorized for a user.

At block 906, in at least one of the various embodiments, access point permission information may be communicated to the biometric device based on the user's profile. In at least one of the various embodiments, during the authorization of the biometric device the AAD may be arranged to retrieve information about which access points the user may be enabled to access. In at least one of the various embodiments, the information may be in the form of a list of restricted access points, or it may be a list of accessible access points, or a combination thereof.

In at least one of the various embodiments, the permission information may be configured and stored on a biometric authentication server, an AAD, or the like. In at least one of the various embodiments, permissions may be assigned or allocated on a per user basis, or based on user groups, user roles, or other user properties. In at least one of the various embodiments, the permissions may be included as part of a biometric profile for a user.

In at least one of the various embodiments, the permission information may enable an administrator to configure which users may be enabled to access certain access points. See, FIGS. 13-15. Importantly, in at least one of the various embodiments, the permissions may be managed outside of the access point. Accordingly, in at least one of the various embodiments, the access point may be relieved of any responsibility to manage if an authorized/identified user actually has permission to access a particular access point.

At block 908, in at least one of the various embodiments, the authenticated biometric device encounters an access point. In at least one of the various embodiments, the biometric device and the access point may recognize each other's presence. For example, in at least one of the various embodiments, a wireless protocol such as Bluetooth's advertising protocol may be employed to enable the biometric device and the access point to identify each other.

In at least one of the various embodiments, the biometric device and the access point may be begin a handshaking protocol (e.g., exchanging control signals) for determining if the biometric device is authenticated with its wearer and preauthorized.

At decision block 910, in at least one of the various embodiments, if access to the access point is allows based on the user profile and the access point profile, control may flow block 912; otherwise, control may flow to block 910. In at least one of the various embodiments, before the biometric device communicates its authentication status to the access point the permission information onboard the biometric device may be checked to determine if the user wearing the biometric device should be enable to access the access point. In at least one of the various embodiments, the biometric device and/or the access point may employ the user's profile or the access point's profile (if any) for determining if the authenticated and preauthorized user can obtain access to the access point.

In at least one of the various embodiments, the user profile information, or a portion of it, may be located on the biometric device, or stored on a biometric authentication server accessible over a network. Likewise, in at least one of the various embodiments, the access point profile information, or a portion of it, may be located on the access point, or stored on a biometric authentication server accessible over a network. In at least one of the various embodiments, user profile information and/or access point profile information may be accessible from a cloud based service.

In at least one of the various embodiments, the authenticated biometric device authenticates the identity of the user that is wearing the device, but it may indicate if that particular user is allowed access to the access point.

In at least one of the various embodiments, the access point may maintain permission information regarding the authenticated users that may be enabled access. However, for some access points, especially those designed to be low powered and/or without network connectivity, they may not have facilities sufficient for determining if a user, even though authenticated by the wearable biometric, is authorized to access the access point.

For example, in at least one of the various embodiments, each member of a family comprising adult and children may use wearable biometric device. The biometric devices may authenticate the identification each member of the family, adult and child alike. However, in this example, it may be important to restrict the children from accessing particular access points. For example, an access point like an automobile door or an automobile ignition may be restricted to just the authenticated adults.

Accordingly, rather than requiring the automobile access points to maintain an access control list that distinguishes among family members, the biometric device for the children may maintain the permission information. This permission information may be updated for an individual each time a user authenticates with given biometric device. Returning the last example, if a child obtains his or her driver's license the parents may update the child's permission information, enabling them to use their biometric device to enable access the automobile. Note, this may be accomplished without directly updating the automobile access point.

At block 912, in at least one of the various embodiments, since the access point is not accessible to the user, access to the access point may be denied for the user. Next, control may flow to a return block to return control to a calling process. During the handshaking between the biometric device and the access point, the biometric device reject the access point control signals, or it may be arranged to refrain from sending an "authenticated" status to the access point. At block 914, in at least one of the various embodiments, since access to the access point is permitted list, or otherwise not barred for the user, access to the access point may be enabled. Next, control may be returned to a calling process.

Figure 10:
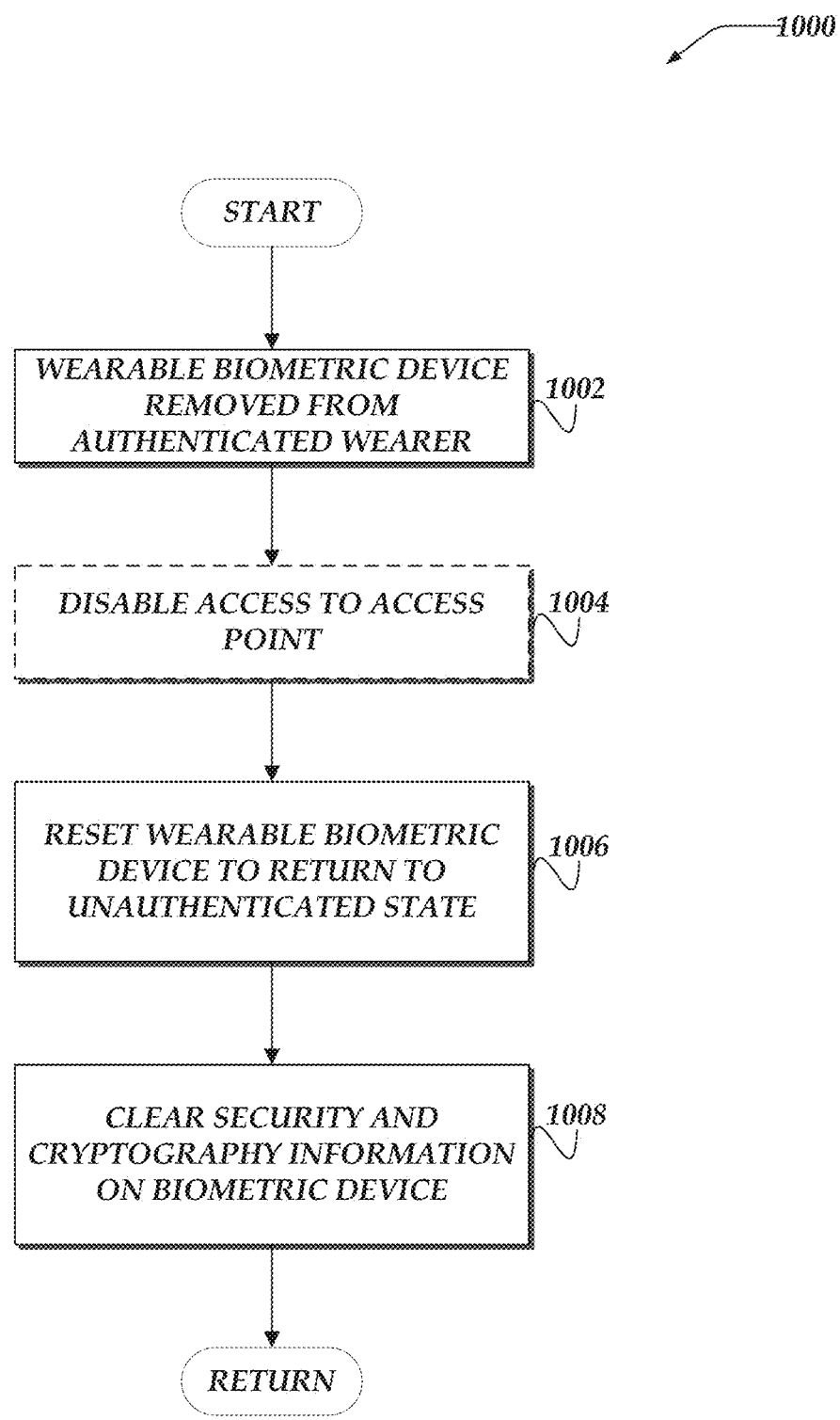
FIG. 10 shows an overview flowchart for a process for de-authenticating a biometric device when it is removed from a wearer in accordance with at least one of the various embodiments.

FIG. 10 shows an overview flowchart for process 1000 de-authenticating a biometric device when it is removed from a wearer in accordance with at least one of the various embodiments. After a start block, at block 1002, in at least one of the various embodiments, a wearable biometric device is removed from an authenticated wearer. In at least one of the various embodiments, the biometric device may detect that has been removed, or is about to be removed (e.g., clasp opening) from the authenticated user as described above. Also, In at least one of the various embodiments, the biometric device may include a lanyard attached by a clasp such that removing the lanyard from the biometric device resets (deauthorizes/deauthenticates) the biometric device.

In at least one of the various embodiments, the biometric device may remain preauthorized and authenticated as long it remains within a defined range/proximity of the user. Additional sensors or radios on the user's person may be employed to determine if the biometric device is within an allowed range of user. For example, a user may preauthorize a handheld tool or device using biometric features. Then as long as the preauthorized device remains with a range defined range of the user it will remain preauthorized—enabling the tool to be used by the user.

At block 1004, in at least one of the various embodiments, optionally, access to one or more access points may be disabled. In at least one of the various embodiments, if the biometric device is being employed to enable the user to access an access point, the access point may be configured to automatically disable access to the access point. In at least one of the various embodiments, in some cases, such as, an operating automobile, the access point may be configured to continue operating until it is safe to disable operation. In other cases, such as, accessing a secure terminal the access point may immediately disable access for the current user. In at least one of the various embodiments, other configuration may include starting a countdown timer before disabling access. Also, the access point may be configured to generate a log entry and/or generate a notification upon removal of the biometric device. Note, in at least one of the various embodiments, this block may be considered optional because the user may not be accessing an access point when the biometric device is removed.

At block 1006, in at least one of the various embodiments, the wearable biometric device may be reset and set to an unauthenticated state. In at least one of the various embodiments, as discussed above, resetting the biometric device will require a user to authenticate biometric device again by providing biometric information to the AAD and matching the biometric profile that corresponds to the user before the biometric device returned to an authenticated state. At block 1008, in at least one of the various embodiments, further to resetting the wearable biometric device, security and cryptographic information related to the operation and/or authentication of the biometric device may be cleared or otherwise erased from the biometric device. Next, control may be returned to a calling process.

Figure 11:
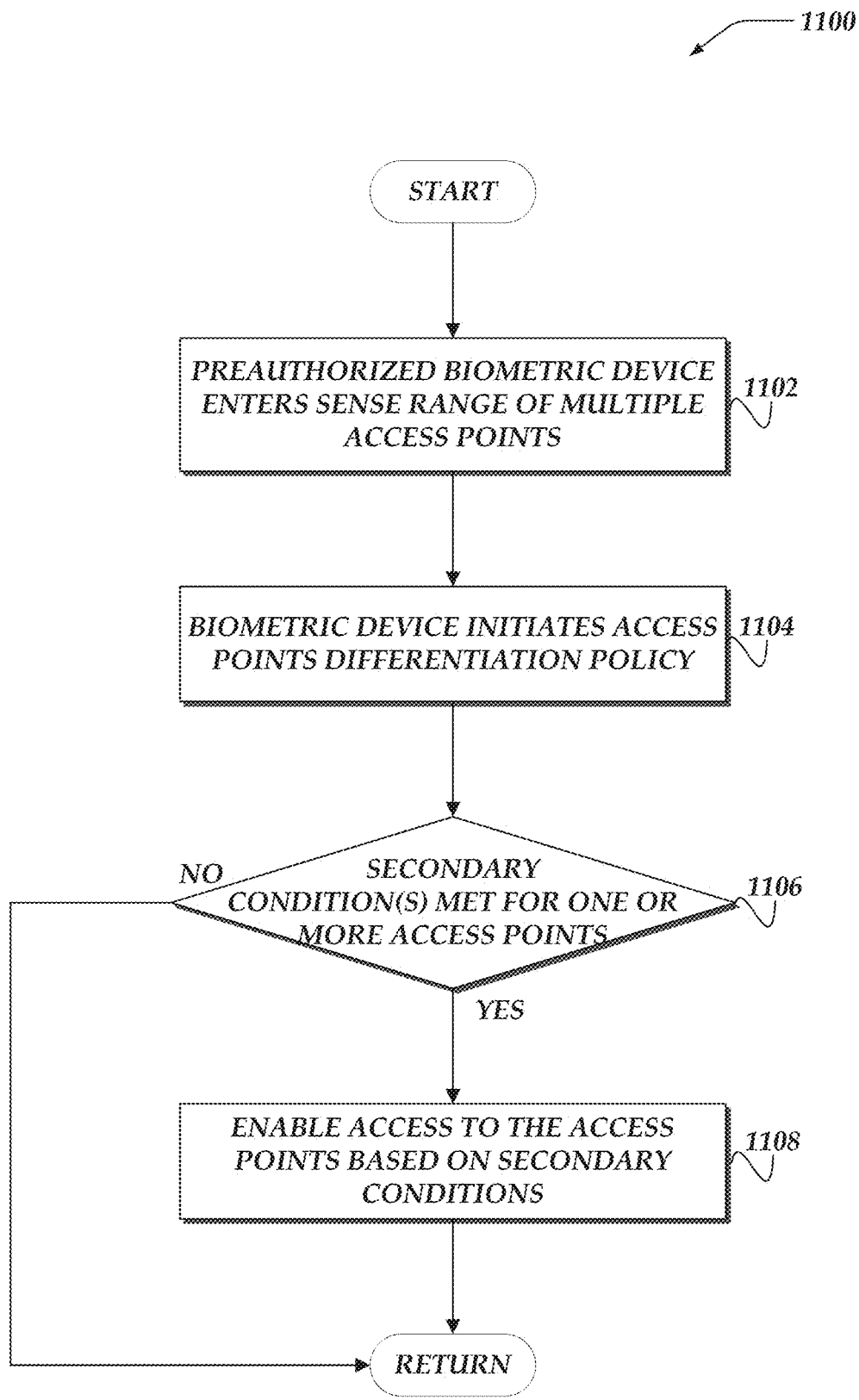
FIG. 11 shows an overview flowchart for a process that manages if a biometric device encounters multiple access points in accordance with at least one of the various embodiments.

FIG. 11 shows an overview flowchart for process 1100 that manages if a biometric device encounters multiple access points in accordance with at least one of the various embodiments. After a start block, at block 1102, in at least one of the various embodiments, an authenticated biometric device enters the sensing range of multiple access points. In at least one of the various embodiments, a user wearing an authenticated biometric device may walk into a room with several access points that he or she may be enabled to access. For example, in at least one of the various embodiments, a supervisor that enters a room with several access points may not want multiple access points are in range of the wearable biometric device to enable access at the same time.

At block 1104, in at least one of the various embodiments, the biometric device initiates one or more access differentiation policies. In at least one of the various embodiments, since the biometric device has sensed multiple access points at the same time it may be configured to execute one or more differentiation policies.

In at least one of the various embodiments, differentiation policies may be configured to have different rules for different classifications of access points. In some embodiments, for some types of access points, it may be unnecessary to distinguish between them. For example, if the multiple access points correspond to room light switches it may be harmless and/or desirable to turn all the switches on when a user wearing an authenticated biometric device enters a room. However, in other cases, such as, computer terminals it may be undesirable to unlock and enable access to each detected terminal at the same time.

Accordingly, in at least one of the various embodiments, the differentiation policy may include rules and filters that may be associated with the various access point that may be encountered. In at least one of the various embodiments, the differentiation policies may be established one or more secondary conditions that must be met to differentiate among certain multiple access points.

In at least one of the various embodiments, secondary conditions may be similar to those described above, such as, requiring PINs, passwords, proximity requirements, gestures, or the like, with respect to the particular access point the user wants to access.

At decision block 1106, in at least one of the various embodiments, if one or more secondary conditions are met for differentiating among access points, control may flow to block 1108; otherwise, control may flow to a return block. In at least one of the various embodiments, if the secondary conditions are not met, access to those access points requiring the secondary conditions may remain disabled. At block 1108, in at least one of the various embodiments, access to one or more access points may be enabled based on the secondary conditions that may have been met. Next, control may be returned to a calling process.

Figure 12:
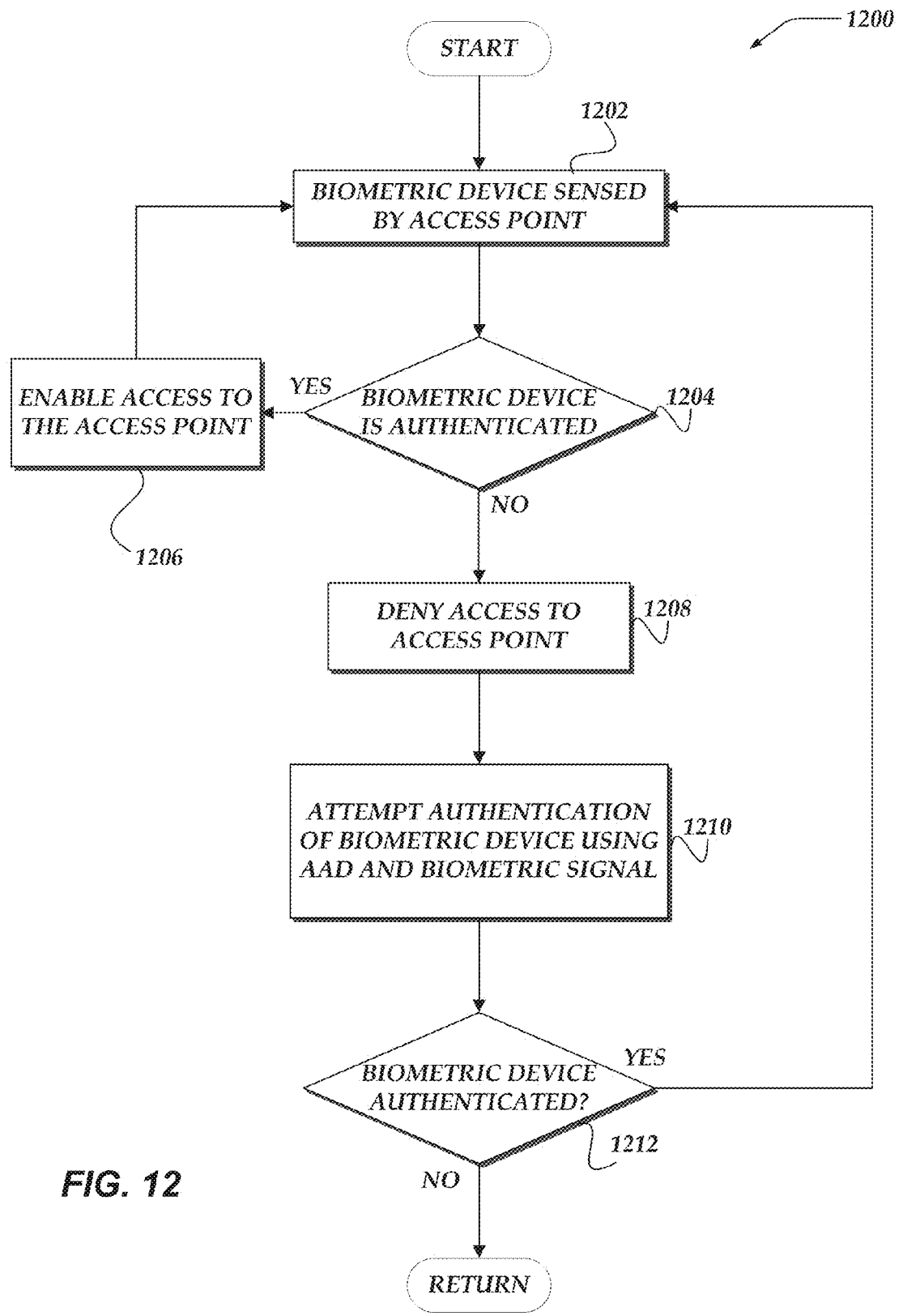
FIG. 12 shows an overview flowchart for a process for authenticating a biometric device during encounters with access points in accordance with at least one of the various embodiments.

FIG. 12 shows an overview flowchart for process 1200 for authenticating a biometric device during encounters with access points in accordance with at least one of the various embodiments. After a start block, at block 1202, in at least one of the various embodiments, a biometric device may be sensed by an access point. Further, in at least one of the various embodiments, the biometric device may sense one or more access points that are within range of its radios. As discussed above, one or more features of radios and/or wireless facilities on the biometric devices and the access points may be employed for sensing each other's presence. For example, one or more wireless advertising protocols may be employed by the biometric devices and/or the access points. Accordingly, each time a user with an active biometric device encounters an access point control signals may be exchanged between the biometric device and the access point.

At decision block 1204, in at least one of the various embodiments, if a biometric device is authenticated, control may flow to block 1206; otherwise control may flow to block 1208. In at least one of the various embodiments, if the biometric device is preauthorized for the user, the access point may assume that the biometric device is authenticated and authorized for the user and enable access to the access point (e.g., confirming that the biometric device is in an authenticated state). Note, access the access point may be enabled without having to capture additional biometric signals or information from the user. Thus, in at least one of the various embodiments, the user may be enabled to access multiple access points at different times as long as the biometric device remains in an authenticated state (e.g., as long as the biometric device has not been removed or separated from the authenticated user).

At block 1206, in at least one of the various embodiments, access to the encountered access point may be enabled. Next, control may loop back to block 1202. Accordingly, in at least one of the various embodiments, process 1200 may continue sensing access points and enabling access to them based on the authenticated status of the preauthorized biometric device.

At block 1208, in at least one of the various embodiments, since the biometric device is not authenticated or preauthorized, access to the encountered access point may be denied. In at least one of the various embodiments, as discussed above a biometric device may become unauthenticated if previously authenticated user removes the preauthorized biometric device. Also, as discussed above, in at least one of the various embodiments, a biometric device may be configured to require periodic re-authentication even though the user has not removed the device.

At block 1210, in at least one of the various embodiments, the biometric device may attempt to authenticate using an AAD and one or more biometric signals captured from the user. In at least one of the various embodiments, since the biometric device is not authenticated with the user, the user may proceed to perform the actions to put the biometric device into an authenticated state and preauthorized status, as discussed in detail above.

At decision block 1212, in at least one of the various embodiments, if the attempt to authenticate and preauthorize the biometric device succeeds, control may flow to block 1202; otherwise, process 1200 may exit, returning control to a calling process. Assuming that the biometric device is preauthorized and authenticated by the user, process 1200 may loop back to block 1202 to continue sensing access points.

Figure 13:
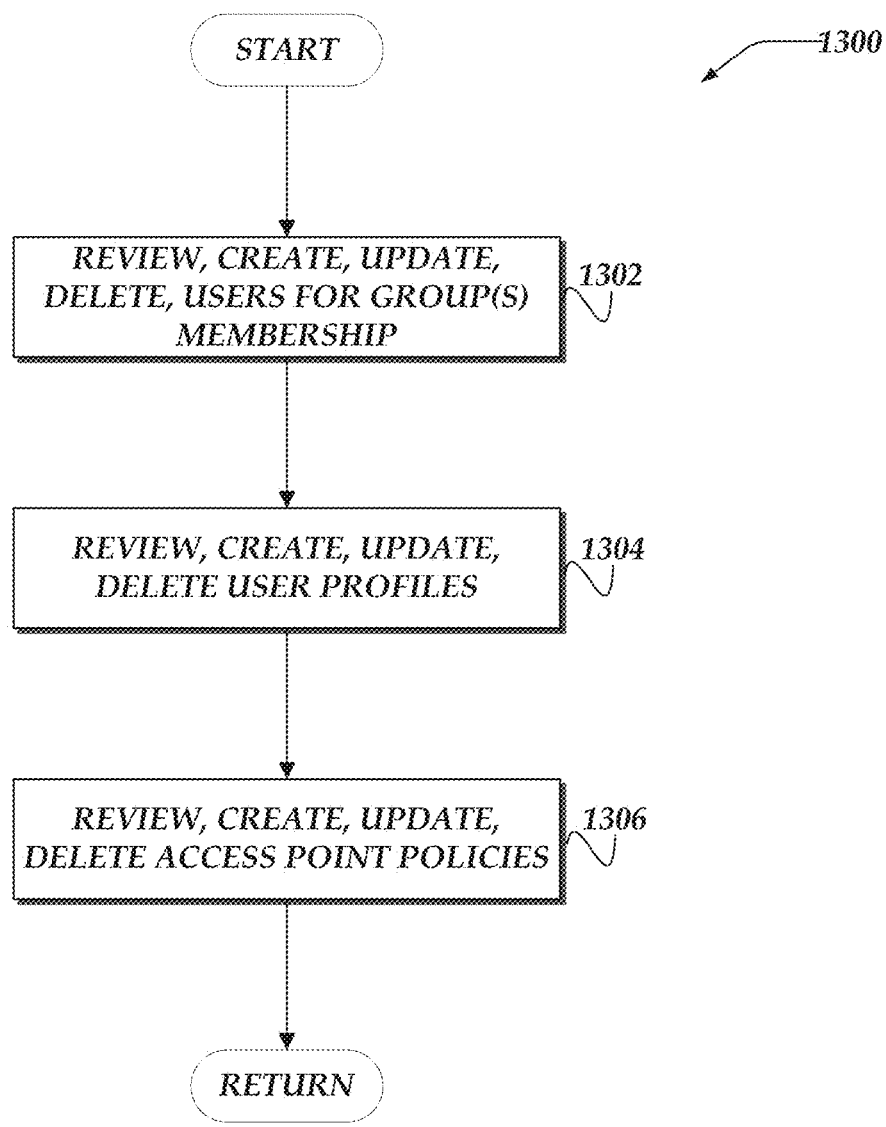
FIG. 13 shows an overview flowchart for a process for configuring profiles for users and access points in accordance with at least one of the various embodiments.

FIG. 13 shows an overview flowchart for process 1300 for configuring profiles for users and access points in accordance with at least one of the various embodiments. After a start block, at block 1302, in at least one of the various embodiments, an administrative user may review, create, update, or delete users associated with one or more groups. At block 1304, in at least one of the various embodiments, the administrative user may review, create, update, or delete, one or more of the user profiles. At block 1306, in at least one of the various embodiments, the administrative user may review, create, update, or delete, one or more access points. Next, control may be returned to a calling process.

In at least one of the various embodiments, biometric devices may be employed to authenticate the identity of users wearing or otherwise in control of the biometric device. Further, an organization, such as, an employer, an entertainment vendor, amusement park operator, or the like, may provide or issue biometric metrics to users, such as, employees, visitors, customers, or the like. Also, in at least one of the various embodiments, a head of household for a family may issue biometric devices for each member of the family.

Accordingly, in at least one of the various embodiments, administrative users may generate user profiles that include configuration rules or other information that may be employed for determining if an authenticated and/or preauthorized user may indeed be allowed to obtain access to an access point. For example, in at least one of the various embodiments, if each member of a family has been issued biometric devices, it follows that in many cases, not each family will have the access to same access points as each. For example, under age children of the family may be disabled from accessing certain access points, such as, the family automobile or banking information. Likewise, in at least one of the various embodiments, employers that issue biometric devices to their employees may employ user profiles and/or access profiles to control access to access points for employees. Further, in at least one of the various embodiments, amusement park operators may issue biometric devices that may be employed to enable or disable customers from obtaining access to various rides, events, attractions, and so on that may be hosted at the amusement park.

In at least one of the various embodiments, profile information may be generated using one or more predefined forms and/or property sheets. Also, in at least one of the various embodiments, profile information may include customized rules that may be comprised of one or more regular expression, computer software programming languages, scripts, or the like, or combination thereof.

Figure 14:
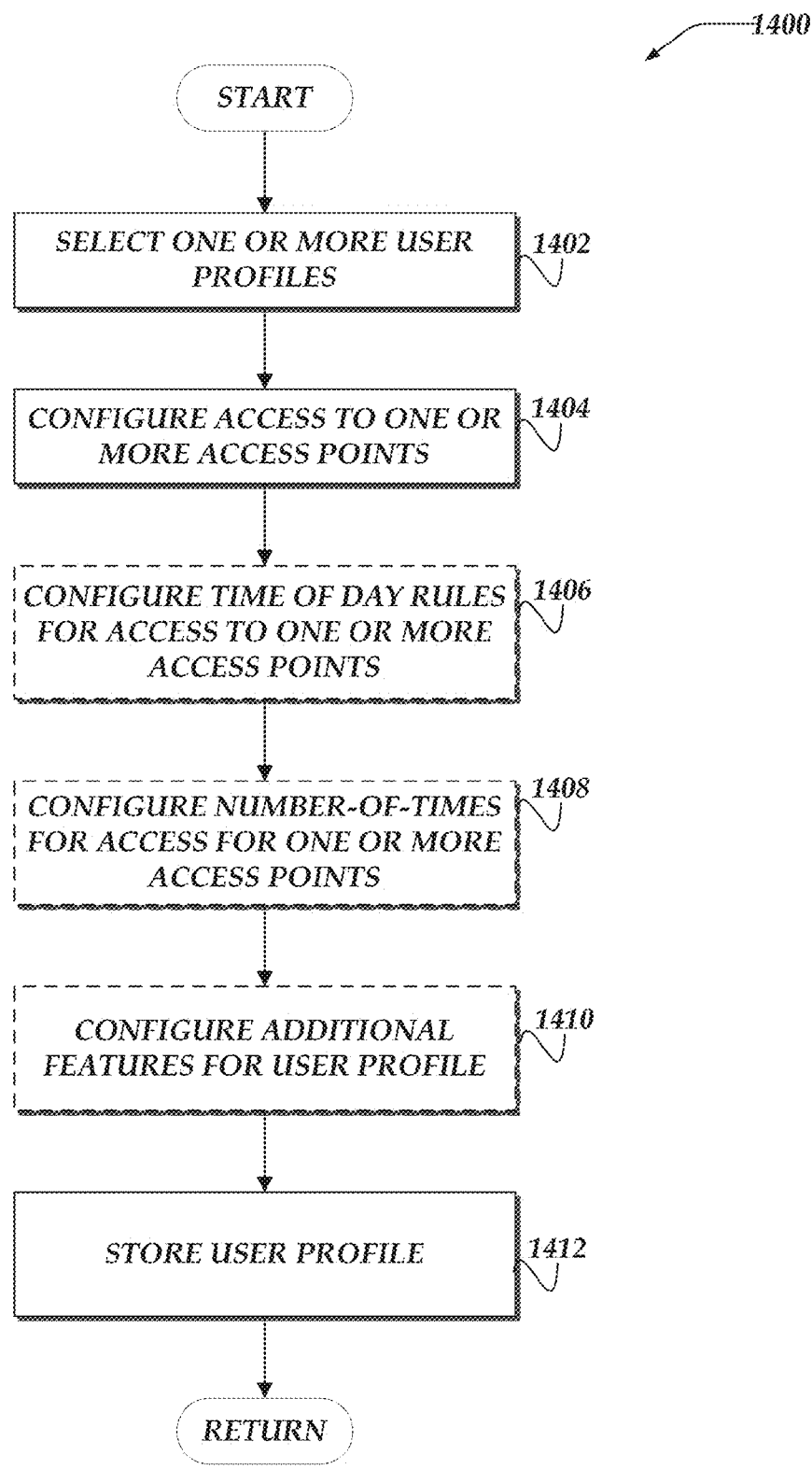
FIG. 14 shows an overview flowchart for a process for configuring profiles for users in accordance with at least one of the various embodiments.

FIG. 14 shows an overview flowchart for process 1400 for configuring profiles for users in accordance with at least one of the various embodiments. After a start block, at block 1402, in at least one of the various embodiments, an administrative user may select one or more user profiles. In at least one of the various embodiments, user profiles may be selected individually or in groups using bulk selections, filters, or the like. Also, in at least one of the various embodiments, portions of one or more user profiles may be shared by one or more user points. For example, a global user profile may provide base configuration information each employee in a company.

At block 1404, in at least one of the various embodiments, the user profile may be configured to enable access for the user to one or more access points. In at least one of the various embodiments, individual access point and/or groups of access points may be black listed or white lists for one or more users. This information may be included in, or associated with, the user profile for each user.

At block 1406, in at least one of the various embodiments, optionally, the user profile may be configured to enable access for the user to one or more access points based on date, time of day, day-of-week, or the like, or combination thereof.

At block 1408, in at least one of the various embodiments, optionally, the user profile may be configured to define one or more count based limits for enabling the user access to one or more access points. In at least one of the various embodiments, these may be numerical limits to control the number of times an individual may access an access point. In other embodiments, the limits may be constrained to one or more time periods or time ranges. For example, a user may be restricted to accessing a particular access point one time during a defined period of time while the same user may be configured for unlimited access at other times.

At block 1410, in at least one of the various embodiments, optionally, the user profile may be configured to enable or disable one or more additional features related enabling the user access one or more access points. For example: a user may be restricted or enabled access to access points based on geolocation; a number of other users currently accessing the same or different access points exceeding a threshold; a number of other users that have accessed the same or different access points in a defined time period exceeding a threshold; or the like; or combination thereof.

At block 1410, in at least one of the various embodiments, the configured user profile may be stored. In at least one of the various embodiments, the configured user profiles may be stored in one or more computers, such as, biometric authentication service computer 116, a compute and/or storage instance (e.g., virtual machine) in cloud service and/or cloud environment, or the like. One of ordinary skill the art will appreciate that user profile configuration rules may include enabling and disabling access to access points for the user based on numerous features and/or conditions beyond those described herein. Such configuration rules are in envisaged, however, in the interest of brevity and clarity the examples are limited herein. However, the example are sufficient for enabling one of ordinary skill in the art to understand and practice the innovations included herein. Next, control may be returned to a calling process.

Figure 15:
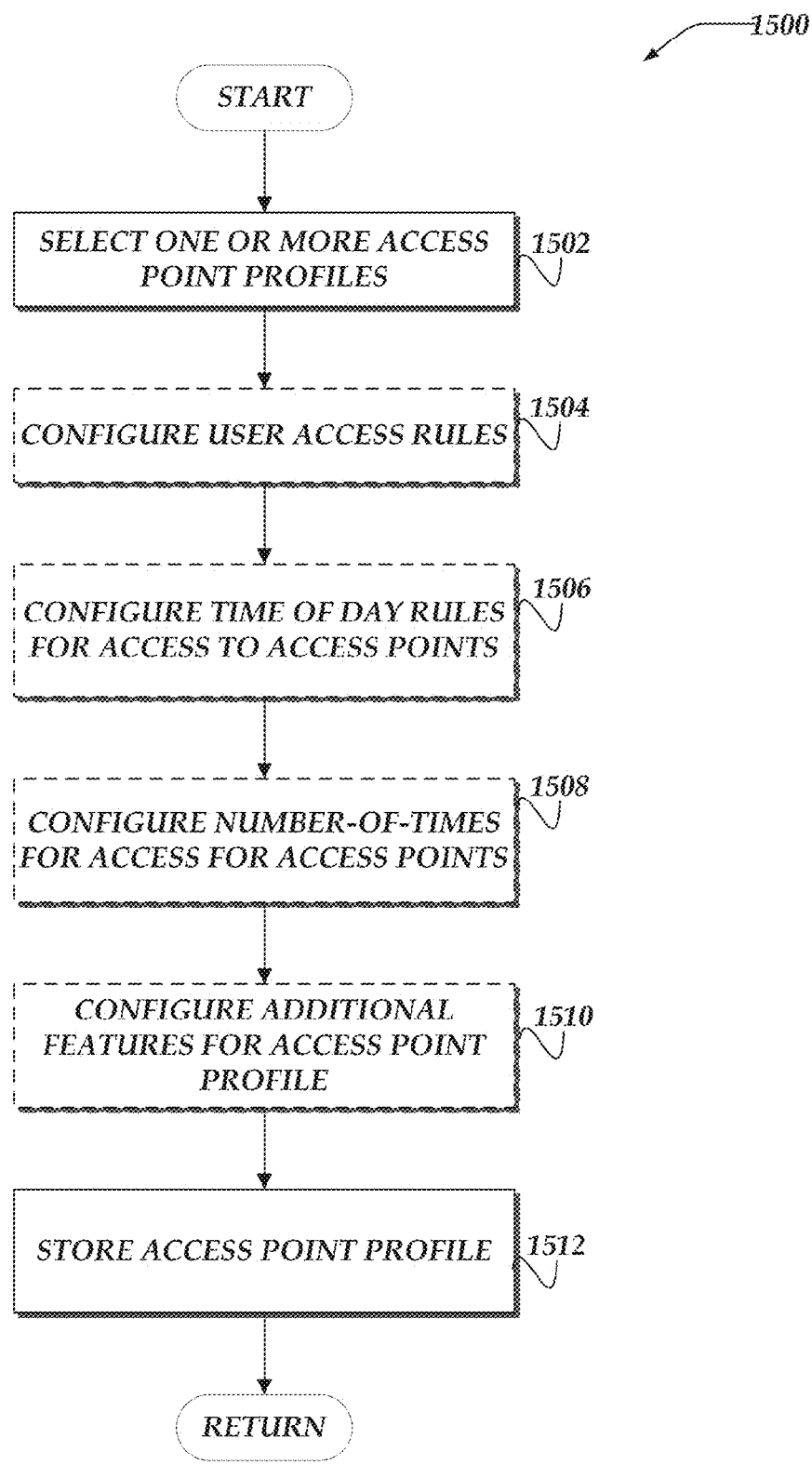
FIG. 15 shows an overview flowchart for a process for configuring profiles for access points in accordance with at least one of the various embodiments.

FIG. 15 shows an overview flowchart for process 1500 for configuring profiles for access points in accordance with at least one of the various embodiments. After a start block, at block 1502, an administrative user may select one or more access point profiles. In at least one of the various embodiments, access point profiles may be selected individually or in groups using bulk selections, filters, or the like. Also, in at least one of the various embodiments, one or more access point profiles may be shared by one or more access points.

At block 1504, in at least one of the various embodiments, optionally, the administrative user may configure rules for determining which users may access the access points. In at least one of the various embodiments, users may be whitelisted or black listed based on individual identity, filters, group rules, or the like. In at least one of the various embodiments, filters may be inclusive or exclusive. Further, in some embodiments filters may be targeted to one or more of the various properties of users and/or user profiles, such as, name, age, access level, security clearance, frequency of access, or the like, or combination thereof.

At block 1506, in at least one of the various embodiments, optionally, the administrative user may configure time of day rules for the access points. Similar as described for block 1406 in FIG. 14. Likewise, at block 1508, in at least one of the various embodiments, optionally, the administrative user may configure policy rules for access based on number-of-times, similar as described for block 1408 in FIG. 14. At block 1510, in at least one of the various embodiments, optionally, the administrative user may configure one or more additional policy rules based on one or more other features/properties associated with the access points—similar to block 1410 in FIG. 14.

At block 1512, in at least one of the various embodiments, optionally, the administrative user may store the access point profiles. In at least one of the various embodiments, the configured access point profiles may be stored in one or more computers, such as, biometric authentication service computer 116, a compute and/or storage instance (e.g., virtual machine) in cloud service and/or cloud environment, or the like. One of ordinary skill the art will appreciate that access point profile configuration rules may include enabling and disabling access to access points for users based on numerous features and/or conditions beyond those described herein. These and other additional configuration rules are envisaged, however, in the interest of brevity and clarity the examples include herein are limited in number. However, the provided examples are sufficient for enabling one of ordinary skill in the art to understand and practice these innovations. Next, control may be returned to a calling process.

It will be understood that each block of the flowchart illustration, and combinations of blocks in the flowchart illustration, may be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer-implemented process such that the instructions, which execute on the processor to provide steps for implementing the actions specified in the flowchart block or blocks. The computer program instructions may also cause at least some of the operational steps shown in the blocks of the flowchart to be performed in parallel. These program instructions may be stored on some type of machine readable storage media, such as processor readable non-transitive storage media, or the like. Moreover, some of the steps may also be performed across more than one processor, such as might arise in a multi-processor computer system. In addition, one or more blocks or combinations of blocks in the flowchart illustration may also be performed concurrently with other blocks or combinations of blocks, or even in a different sequence than illustrated without departing from the scope or spirit of the invention.

Accordingly, blocks of the flowchart illustration support combinations of means for performing the specified actions, combinations of steps for performing the specified actions and program instruction means for performing the specified actions. It will also be understood that each block of the flowchart illustration, and combinations of blocks in the flowchart illustration, may be implemented by special purpose hardware-based systems, which perform the specified actions or steps, or combinations of special purpose hardware and computer instructions. The foregoing example should not be construed as limiting and/or exhaustive, but rather, an illustrative use case to show an implementation of at least one of the various embodiments of the invention.

Illustrative Use Cases

Figure 16:
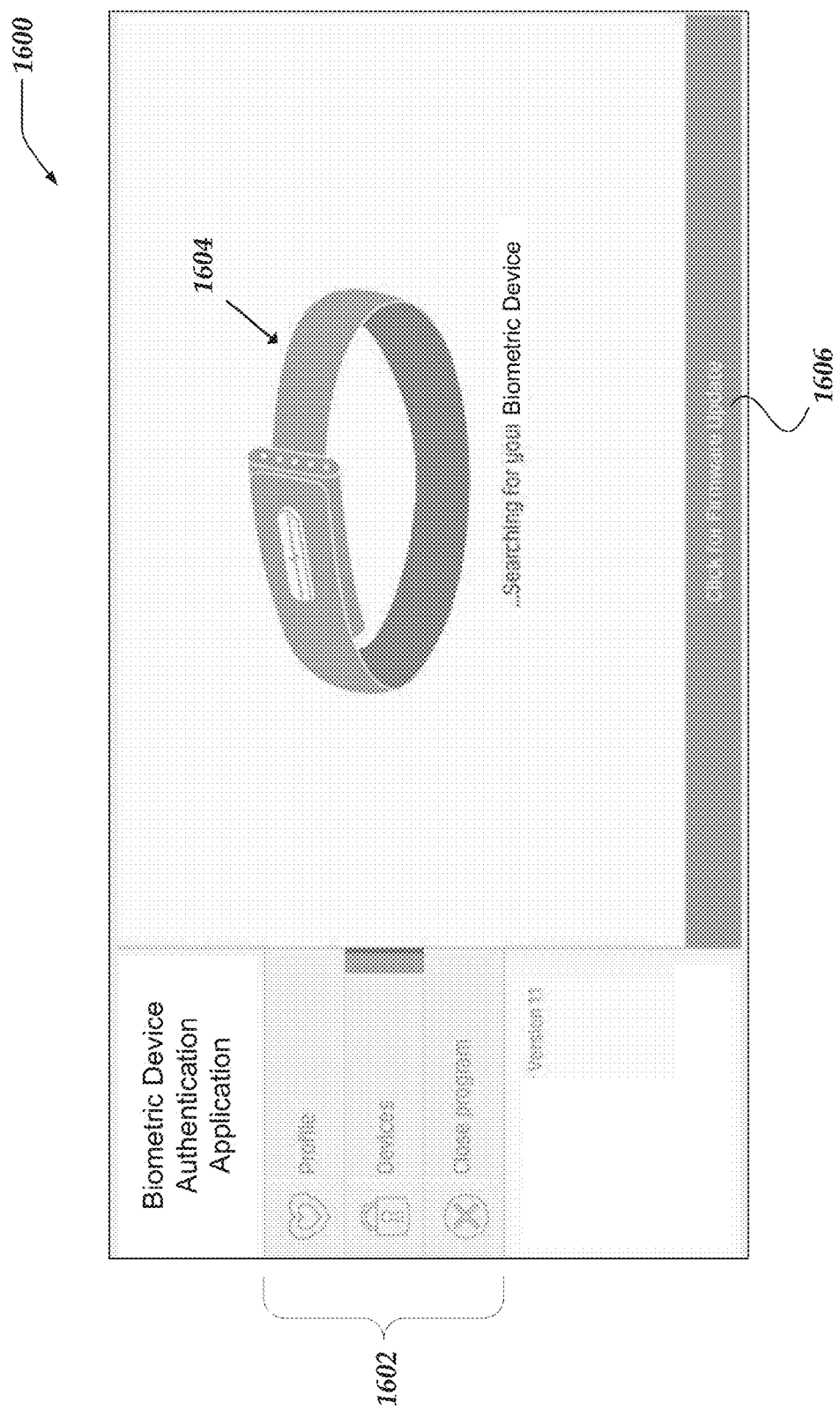
FIG. 16 illustrates a portion of a user interface for enrolling and/or configuring a biometric device in accordance with at least one of the various embodiments.

FIG. 16 illustrates a portion of user interface 1600 for enrolling and/or configuring a biometric device in accordance with at least one of the various embodiments. In at least one of the various embodiments, an AAD and/or a biometric authentication server may be arranged to include one or more user interfaces that enable a user to enroll and/or configure their biometric devices. In at least one of the various embodiments, user interface 1600 may include a representation of the biometric device(s) such as biometric device image 1602, as well as one or more menu items for configuration such devices, such as, menu items 1604. Further, in some embodiments, a user may be enabled to update the software and/or firmware for their biometric devices by activating a user interface input, such as, button 1606.

In at least one of the various embodiments, the user interface layout and features may be arranged to accommodate different platforms, such as, client computers, network computers, mobile computers, tablet computers, smart phones, or the like. Further, in at least one of the various embodiments, user interfaces may include more or less elements as shown herein and remain within the scope of the envisaged innovations.

Figure 17:
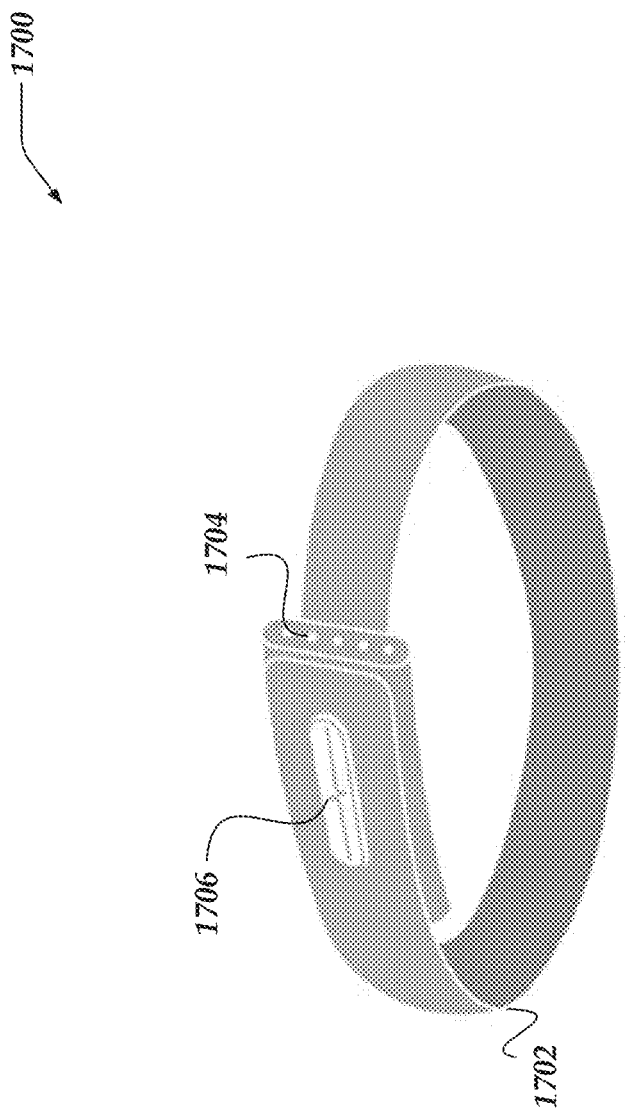
FIG. 17 illustrates a wearable biometric device in accordance with at least one of the various embodiments. In at least one of the various embodiments.

FIG. 17 illustrates wearable biometric device 1700 in accordance with at least one of the various embodiments. In at least one of the various embodiments, biometric device 1700 may be arranged in the form a wristband, such as, wristband 1702. Also, in at least one of the various embodiments, biometric device 1700 may include LED's 1704 arranged such that they are visible to a wearer.

In at least one of the various embodiments, LEDs 1704 may be arranged to flash in different patterns and/or colors. In some embodiments, the different patterns of flashing and/or colors may correspond to particular operations, states, actions, or the like. For example, unique flashing or light patterns may be established to represent if the biometric device is capturing and/or transmitting biometric signals/data. Also, for example, a particular LED pattern may indicate if the biometric device is authenticated, preauthorized, in the range of one or more access points, or the like.

In at least one of the various embodiments, contact 1706 may be a button, sensor, electrode, or the like, or combination thereof. In some embodiments, contact 1706 may be a sensor similar to sensor 504 in FIG. 5. In at least one of the various embodiments, contact 1706 may be arranged to be sensitive to receiving user inputs such as finger tapping, finger swiping, touching, or the like, or combination thereof.

What is claimed as new and desired to be protected by Letters Patent of the United States is:

1. A method for authenticating a user using a device that performs actions including:
   capturing unique information that identifies the user of the device;
   authenticating the user of the device based on the information, wherein the authentication includes:
      communicating the information to an authorized authentication device (AAD) that is included with the device; and
      comparing the information to a profile that corresponds to the user and is stored on the AAD, wherein the AAD preauthorizes the device for the user when the profile stored on the AAD corresponds to the information; and
   providing the preauthorization to one or more access points, wherein the user is provided access to the one or more access points based on the preauthorization of the device.

2. The method of claim 1, wherein the information further comprises one or more of a voice command, a finger tap, a finger swipe, a distance between the preauthorized device and the one or more access points, or additional information that identifies the user.

3. The method of claim 1, wherein the device further comprises one or more notification devices, wherein the one or more notification devices include a vibrator or a light emitting device, and wherein the one or more notification devices provide one or more alerts to a user based on one or more events that include when the device is in an authenticated state, when the device is communicating with another device, when the device senses motion, or when a message is received by the device.

4. The method of claim 1, wherein the information further comprises biometric information that includes one or more of a gait, a heart rate, a galvanic skin response, a temperature, a fingerprint, a voiceprint, a body electrical characteristic, a body thermal characteristic, an iris pattern, a vein pattern, an eye vein pattern, a facial structure, a non-facial anatomical structure, an electrocardiogram, an aphotoplethysmogram, an electromyogram, an electroencephalogram, a transient otoacoustic emissions, a phonocardiogram, a DNA, a chemical marker, a biochemical marker, a skin-color variation, a skin-color discolouration, a tattoo, or perspiration.

5. The method of claim 1, wherein the device further comprises one or more sensors, including a motion sensor, a proximity sensor, a barometric sensor, a pressure sensor, a thermometer, a microphone, an infrared sensor, a light sensor, a gyroscope, a Global Positioning System (GPS) transceiver, a manometer, a camera, a humidity sensor, a capacitive sensor, a hall sensor, a galvanic skin sensor, a photoplethysmography sensor, an electroencephalogram sensor, an electromyogram sensor, a blood flow sensor, a bio-impedance sensor, an altimeter sensor, optical sensor, or an UltraViolet light sensor.

6. The method of claim 1, further comprising when the device is detected to be removed from the user, de-authorizing the device for the user, wherein the removal detection includes one or more of electronic conductivity detection, heat flux detection, a galvanic skin response detection, motion detection, periodic biometric signal detection, continuous biometric signal detection, pulse detection, skin temperature detection, ambient temperature detection, blood flow detection, pressure detection, ambient light detection, electromagnetic field detection, respiration detection, heart rate detection, electrocardiogram detection, photoplethysmogram detection, electromyogram detection, electroencephalogram detection, near infra-red detection, skin-color detection, close magnetic contact detection, or a mechanical switch detection.

7. The method of claim 1, further comprises, providing a user interface that includes, one or more of a keyboard, a liquid crystal display (LCD), a light emitting diode (LED) display, an organic LED (OLED) display, a speaker, a microphone, a mouse, a stylus, a virtual button, an electronic button.

8. The method of claim 1, further comprising:
   enabling an administrative user to provide profile information for a plurality of users of the device;
   when one of the plurality of users is wearing the device, authenticating that user based on captured information that identifies that user; and
   providing access to the one or more access points based at least on the provided profile information for the authenticated one of the plurality of users.

9. A device for authenticating a user, comprising:
   a transceiver that communicates over a network;
   a memory that stores at least instructions; and
   one or more processor devices that executes instructions that enable actions, including:
      capturing unique information that identifies the user of the device;
      authenticating the user of the device based on the information, wherein the authentication includes:
         communicating the information to an authorized authentication device (AAD) that is included with the device; and
         comparing the information to a profile that corresponds to the user and is stored on the AAD, wherein the AAD preauthorizes the device for the user when the profile stored on the AAD corresponds to the information; and providing the preauthorization to one or more access points, wherein the user is provided access to the one or more access points based on the preauthorization of the device.

10. The device of claim 9, wherein the information further comprises one or more of a voice command, a finger tap, a finger swipe, a distance between the preauthorized device and the one or more access points, or additional information that identifies the user.

11. The device of claim 9, wherein the device further comprises one or more notification devices, wherein the one or more notification devices include a vibrator or a light emitting device, and wherein the one or more notification devices provide one or more alerts to a user based on one or more events that include when the device is in an authenticated state, when the device is communicating with another device, when the device senses motion, or when a message is received by the device.

12. The device of claim 9, wherein the information further comprises biometric information that includes one or more of a gait, a heart rate, a galvanic skin response, a temperature, a fingerprint, a voiceprint, a body electrical characteristic, a body thermal characteristic, an iris pattern, a vein pattern, an eye vein pattern, a facial structure, a non-facial anatomical structure, an electrocardiogram, a photoplethysmogram, an electromyogram, an electroencephalogram, a transient otoacoustic emissions, a phonocardiogram, a DNA, a chemical marker, a biochemical marker, a skin-color variation, a skin-color discolouration, a tattoo, or perspiration.

13. The device of claim 9, wherein the device further comprises one or more sensors, including a motion sensor, a proximity sensor, a barometric sensor, a pressure sensor, a thermometer, a microphone, an infrared sensor, a light sensor, a gyroscope, a Global Positioning System (GPS) transceiver, a manometer, a camera, a humidity sensor, a capacitive sensor, a hall sensor, a galvanic skin sensor, a photoplethysmography sensor, an electroencephalography sensor, an electromyography sensor, a blood flow sensor, a bio-impedance sensor, an altimeter sensor, optical sensor, or an UltraViolet light sensor.

14. The device of claim 9, further comprising when the device is detected to be removed from the user, de-authorizing the device for the user, wherein the removal detection includes one or more of electronic conductivity detection, heat flux detection, a galvanic skin response detection, motion detection, periodic biometric signal detection, continuous biometric signal detection, pulse detection, skin temperature detection, ambient temperature detection, blood flow detection, pressure detection, ambient light detection, electromagnetic field detection, respiration detection, heart rate detection, electrocardiogram detection, photoplethysmogram detection, electromyogram detection, electroencephalogram detection, near infra-red detection, skin-color detection, close magnetic contact detection, or a mechanical switch detection.

15. The device of claim 9, further comprises, providing a user interface that includes, one or more of a keyboard, a liquid crystal display (LCD), a light emitting diode (LED) display, an organic LED (OLED) display, a speaker, a microphone, a mouse, a stylus, a virtual button, an electronic button.

16. The device of claim 9, further comprising:
enabling an administrative user to provide profile information for a plurality of users of the device;
when one of the plurality of users is wearing the device, authenticating that user based on captured information that identifies that user; and
providing access to the one or more access points based at least on the provided profile information for the authenticated one of the plurality of users.

17. A system for using a device to authenticate a user, comprising:
a device for authenticating a user, comprising:
a transceiver that communicates over a network;
a memory that stores instructions; and
one or more processors that execute the instructions that perform actions, including:
capturing unique information that identifies the user of the device;
authenticating the user of the device based on the information, wherein the authentication includes:
communicating the information to an authorized authentication device (AAD) that is included with the device; and
comparing the information to a profile that corresponds to the user and is stored on the AAD, wherein the AAD preauthorizes the device for the user when the profile stored on the AAD corresponds to the information; and
providing the preauthorization to one or more access points; and
an access point computer, comprising:
a transceiver that communicates over the network;
a memory that stores instructions; and
one or more processors that execute instructions that perform actions, including:
providing the access to the one or more access points to the user based on the preauthorization provided by the device.

18. The system of claim 17, wherein the information further comprises one or more of a voice command, a finger tap, a finger swipe, a distance between the preauthorized device and the one or more access points, or additional information that identifies the user.

19. The system of claim 17, wherein the device further comprises one or more notification devices, wherein the one or more notification devices include a vibrator or a light emitting device, and wherein the one or more notification devices provide one or more alerts to a user based on one or more events that include when the device is in an authenticated state, when the device is communicating with another device, when the device senses motion, or when a message is received by the device.

20. The system of claim 17, wherein the information further comprises biometric information that includes one or more of a gait, a heart rate, a galvanic skin response, a temperature, a fingerprint, a voiceprint, a body electrical characteristic, a body thermal characteristic, an iris pattern, a vein pattern, an eye vein pattern, a facial structure, a non-facial anatomical structure, an electrocardiogram, an aphotoplethysmogram, an electromyogram, an electroencephalogram, a transient otoacoustic emissions, a phonocardiogram, a DNA, a chemical marker, a biochemical marker, a skin-color variation, a skin-color discolouration, a tattoo, or perspiration.

21. The system of claim 17, wherein the device further comprises one or more sensors, including a motion sensor, a proximity sensor, a barometric sensor, a pressure sensor, a thermometer, a microphone, an infrared sensor, a light sensor, a gyroscope, a Global Positioning System (GPS) transceiver, a manometer, a camera, a humidity sensor, a capacitive sensor, a hall sensor, a galvanic skin sensor, a photoplethysmography sensor, an electroencephalogram sensor, an electromyogram sensor, a blood flow sensor, a bio-impedance sensor, an altimeter sensor, optical sensor, or an UltraViolet light sensor.

22. The system of claim 17, further comprising when the device is detected to be removed from the user, de-authorizing the device for the user, wherein the removal detection includes one or more of electronic conductivity detection, heat flux detection, a galvanic skin response detection, motion detection, periodic biometric signal detection, continuous biometric signal detection, pulse detection, skin temperature detection, ambient temperature detection, blood flow detection, pressure detection, ambient light detection, electromagnetic field detection, respiration detection, heart rate detection, electrocardiogram detection, photoplethysmogram detection, electromyogram detection, electroencephalogram detection, near infra-red detection, skin-color detection, close magnetic contact detection, or a mechanical switch detection.

23. The system of claim 17, further comprises, providing a user interface that includes, one or more of a keyboard, a liquid crystal display (LCD), a light emitting diode (LED) display, an organic LED (OLED) display, a speaker, a microphone, a mouse, a stylus, a virtual button, an electronic button.

24. The system of claim 17, further comprising:
enabling an administrative user to provide profile information for a plurality of users of the device;
when one of the plurality of users is wearing the device, authenticating that user based on captured information that identifies that user; and
providing access to the one or more access points based at least on the provided profile information for the authenticated one of the plurality of users.

25. A processor readable non-transitory storage media that includes instructions for using a device to authenticate a user, wherein execution of the instructions by one or more processors performs actions, comprising:
capturing unique information that identifies the user of the device;
authenticating the user of the device based on the information, wherein the authentication includes:
communicating the information to an authorized authentication device (AAD) that is included with the device; and
comparing the information to a profile that corresponds to the user and is stored on the AAD, wherein the AAD preauthorizes the device for the user when the profile stored on the AAD corresponds to the information; and
providing the preauthorization to one or more access points, wherein the user is provided access to the one or more access points based on the preauthorization of the device.

26. The media of claim 25, wherein the information further comprises a voice command, a finger tap, a finger swipe, a distance between the preauthorized device and the one or more access points, or additional information that identifies the user.

27. The media of claim 25, wherein the device further comprises one or more notification devices, wherein the one or more notification devices include a vibrator or a light emitting device, and wherein the one or more notification devices provide one or more alerts to a user based on one or more events that include when the device is in an authenticated state, when the device is communicating with another device, when the device senses motion, or when a message is received by the device.

28. The media of claim 25, wherein the information further comprises biometric information that includes one or more of a gait, a heart rate, a galvanic skin response, a temperature, a fingerprint, a voiceprint, a body electrical characteristic, a body thermal characteristic, an iris pattern, a vein pattern, an eye vein pattern, a facial structure, a non-facial anatomical structure, an electrocardiogram, an aphotoplethysmogram, an electromyogram, an electroencephalogram, a transient otoacoustic emissions, a phonocardiogram, a DNA, a chemical marker, a biochemical marker, a skin-color variation, a skin-color discolouration, a tattoo, or perspiration.

29. The media of claim 25, wherein the device further comprises one or more sensors, including a motion sensor, a proximity sensor, a barometric sensor, a pressure sensor, a thermometer, a microphone, an infrared sensor, a light sensor, a gyroscope, a Global Positioning System (GPS) transceiver, a manometer, a camera, a humidity sensor, a capacitive sensor, a hall sensor, a galvanic skin sensor, a photoplethysmography sensor, an electroencephalogram sensor, an electromyogram sensor, a blood flow sensor, a bio-impedance sensor, an altimeter sensor, optical sensor, or an UltraViolet light sensor.

30. The media of claim 25, further comprising when the device is detected to be removed from the user, de-authorizing the device for the user, wherein the removal detection includes one or more of electronic conductivity detection, heat flux detection, a galvanic skin response detection, motion detection, periodic biometric signal detection, continuous biometric signal detection, pulse detection, skin temperature detection, ambient temperature detection, blood flow detection, pressure detection, ambient light detection, electromagnetic field detection, respiration detection, heart rate detection, electrocardiogram detection, photoplethysmogram detection, electromyogram detection, electroencephalogram detection, near infra-red detection, skin-color detection, close magnetic contact detection, or a mechanical switch detection.

* * * * *